(12) United States Patent
Brown et al.

(10) Patent No.: US 8,729,103 B2
(45) Date of Patent: May 20, 2014

(54) SILENT DESENSITIZERS OF NEURONAL NACHR AND METHODS OF USE THEREOF

(75) Inventors: Milton L. Brown, Brookeville, MD (US); Mikell A. Paige, Fairfax, VA (US); Yingxian Xiao, Potomac, MD (US); Kenneth J. Kellar, Bethesda, MD (US)

(73) Assignee: Georgetown University, Washington, DC (US)

( * ) Notice: Subject to any disclaimer, the term of this patent is extended or adjusted under 35 U.S.C. 154(b) by 215 days.

(21) Appl. No.: 12/994,376

(22) PCT Filed: May 26, 2009

(86) PCT No.: PCT/US2009/045136
§ 371 (c)(1),
(2), (4) Date: Feb. 15, 2011

(87) PCT Pub. No.: WO2009/143507
PCT Pub. Date: Nov. 26, 2009

(65) Prior Publication Data
US 2011/0269733 A1 Nov. 3, 2011

Related U.S. Application Data

(60) Provisional application No. 61/128,721, filed on May 23, 2008.

(51) Int. Cl.
*A61K 31/4439* (2006.01)
*C07D 401/14* (2006.01)

(52) U.S. Cl.
USPC .................................... 514/340; 546/268.4

(58) Field of Classification Search
USPC ...................................... 546/268.4; 514/340
See application file for complete search history.

(56) References Cited

FOREIGN PATENT DOCUMENTS

| | | |
|---|---|---|
| EP | 0 934 308 B1 | 8/2004 |
| WO | WO-01/19817 A2 | 3/2001 |
| WO | WO-2008/011484 A2 | 1/2008 |
| WO | WO-2008/024978 A2 | 2/2008 |
| WO | WO-2010/045212 A2 | 4/2010 |

OTHER PUBLICATIONS

Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice. pp. 949-982.*
Guillory (in Brittain ed.), "Polymorphism in Pharmaceutical Solids. ," NY: Marcel Dekker, Inc., 1999, 1-2, 125-181, 183-226.*
Yu et al., "Physical characterization of, etc.," PSTT, vl. 1(3), 118-127 (1998).*
Vippagunta et al., "Crystalline Solids", Advanced Drug Delivery Reviews 48 (2001) 3-26.*
Dorwald , Side Reactions in Organic Synthesis, 2005, Wiley: VCH Weinheim Preface, pp. 1-15 & Chapter 8, pp. 279-308.*
Lin, N. H. et al., "Synthesis and structure-activity relationships of 5-substituted pyridine analogues of 3-[2-((S)-pyrrolidinyl)methoxy]pyridine, A-84543 A potent nicotinic receptor ligand", *Bioorganic & Medicinal Chemistry Letters*, 11(5):631-633 (Pergamon, Elsevier Science, Great Britain, Mar. 12, 2001).
Supplementary European Search Report from EP 09 75 1735 dated Jul. 21, 2011.
Bunnelle, W. H. et al., "Structure-Activity Studies and Analgesic Efficacy of N-(3-Pyridinyl)-Bridged Bicyclic Diamines, Exceptionally Potent Agonists at Nicotinic Acteylcholine Receptors", *J. Med. Chem.*, 50:3627-3644 (2007).
Gao, Y., et al., "6-Chloro-3-(((1-[$^{11}$C]methyl)-2-(S)-pyrrolidinyl)methoxy)-5-(2-fluoropyridin-4-yl)pyridine ([$^{11}$C]JHU85270), a potent ligand for nicotinic acetylcholine receptor imaging by positron emission tomography", *Applied Radiation and Isotopes*, 65(8):947-951 (2007).
Zhang, Y. et al., "5-Substituted Derivatives of 6-Halogeno-3-((2-(S)-azetidinyl)methoxy)pyridine and 6-Halogeno-3-((2-(S)-pyrrolidinyl)methoxy)pyridine with Low Picomolar Affinity for α4β2 Nicotinic Acetylcholine Receptor and Wide Range of Lipophilicity: Potential Probes for Imaging with Positron Emission Tomography", *J. Med. Chem.*, 47(10):2453-2465 (2004).
International Search Report from PCT/US2009/045136 dated Jan. 21, 2010.

* cited by examiner

*Primary Examiner* — Patricia L Morris
(74) *Attorney, Agent, or Firm* — Dana M. Gordon; Foley Hoag LLP

(57) ABSTRACT

One aspect of the present invention relates to heterocyclic compounds that are ligands for nicotinic acetylcholine receptors. A second aspect of the invention relates to the use of a compound of the invention for modulation of a mammalian nicotinic acetylcholine receptor.

17 Claims, 9 Drawing Sheets

Figure 2
| Compound | MW | clog P | PSA |
|---|---|---|---|
|  | 375.5 | 4.33 | 81.6 |
| 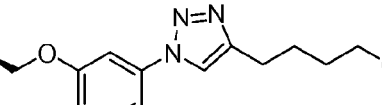 | 355.4 | 2.68 | 100.4 |
|  | 305.4 | 2.06 | 101.0 |
| 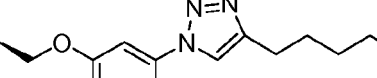 | 342.5 | 4.75 | 28.2 |
| 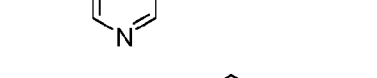 | 343.4 | 3.87 | 50.3 |
| 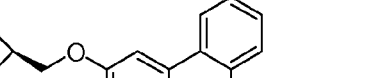 | 332.4 | 4.43 | 37.6 |
| 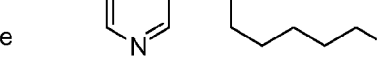 | 348.5 | 4.94 | 40.2 |
| 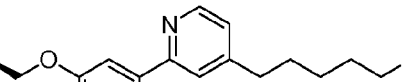 | 331.4 | 4.01 | 47.6 |

| Compound | $K_i$ (nM) | | $\dfrac{\alpha 3\beta 4}{\alpha 4\beta 2}$ | PSA ($\text{Å}^2$) | clog P |
|---|---|---|---|---|---|
| | $\alpha 3\beta 4$ | $\alpha 4\beta 2$ | | | |
| a | 78 ± 10 | 0.14 ± 0.03 | 557 | 59.1 | 0.73 |
| b | 280 ± 30 | 0.059 ± 0.009 | 4,746 | 59.2 | 1.89 |
| c | 6,800 ± 2,300 | 1.6 ± 0.7 | 4,250 | 30.2 | 1.54 |
| d | 23,000 ± 6,000 | 0.93 ± 0.22 | 24,731 | 92.5 | 0.08 |
| e | 63,000 ± 12,000 | 0.85 ± 0.19 | 74,118 | 87.2 | 1.67 |
| f | 88,000 ± 58,000 | 0.95 ± 0.57 | 92,632 | 30.2 | 2.93 |

Figure 7
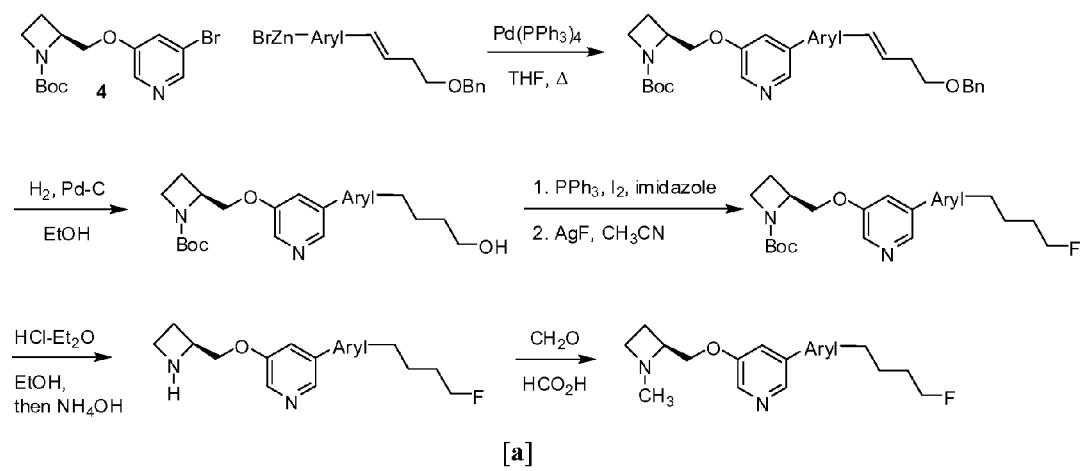
[a]
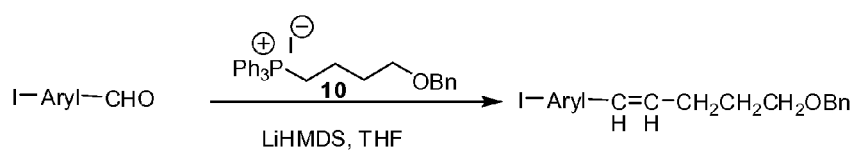
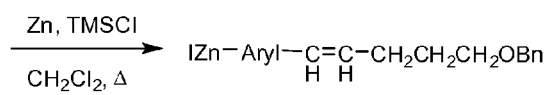
[b]

Figure 8

| Entry | Zinc Reagent | Final Product |
|---|---|---|
| 1 | IZn-[phenyl]-(CH2)4-OBn (ortho) | Azetidine-CH2-O-[pyridine]-[phenyl]-(CH2)4-F (ortho) |
| 2 | IZn-[phenyl]-(CH2)4-OBn (meta) | Azetidine-CH2-O-[pyridine]-[phenyl]-(CH2)4-F (meta) |
| 3 | IZn-[phenyl]-(CH2)4-OBn (para) | Azetidine-CH2-O-[pyridine]-[phenyl]-(CH2)4-F (para) |
| 4 | IZn-[2-pyridyl]-(CH2)4-OBn | Azetidine-CH2-O-[pyridine]-[pyridyl]-(CH2)4-F |
| 5 | IZn-[4-pyridyl]-(CH2)4-OBn | Azetidine-CH2-O-[pyridine]-[pyridyl]-(CH2)4-F |

X=NH, S, or O

| 6 | IZn-[X-heterocycle]-(CH2)4-OBn | Azetidine-CH2-O-[pyridine]-[X-heterocycle]-(CH2)4-F |
| 7 | IZn-[X-heterocycle]-(CH2)4-OBn | Azetidine-CH2-O-[pyridine]-[X-heterocycle]-(CH2)4-F |

| Entry | clog P | | | PSA | | |
|---|---|---|---|---|---|---|
| 1 | 4.75 | | | 28.2 | | |
| 2 | 5.05 | | | 31.3 | | |
| 3 | 5.05 | | | 31.5 | | |
| 4 | 3.87 | | | 50.3 | | |
| 5 | 3.66 | | | 39.5 | | |
| 6 | X= | O | 4.43 | X= | O | 37.6 |
|   |    | S | 4.94 |    | S | 40.2 |
|   |    | NH | 4.01 |   | NH | 47.6 |
| 7 | X= | O | 4.21 | X= | O | 42.8 |
|   |    | S | 4.71 |    | S | 39.2 |
|   |    | NH | 4.01 |   | NH | 55.6 |

SILENT DESENSITIZERS OF NEURONAL NACHR AND METHODS OF USE THEREOF

RELATED APPLICATION

This application claims the benefit of priority to U.S. Provisional Patent Application Ser. No. 61/128,721, filed May 23, 2008; which is hereby incorporated by reference in its entirety.

GOVERNMENT SUPPORT

This invention was made with government support under grant number DA12976 awarded by the National Institutes of Health. The government has certain rights in the invention.

BACKGROUND

The endogenous cholinergic neurotransmitter, acetylcholine (ACh), exerts its biological effect via two types of cholinergic receptors: the muscarinic ACh receptors and the nicotinic acetylcholine receptors (nAChRs). Because muscarinic ACh receptors dominate quantitatively over nAChRs in the brain area important to memory and cognition, much research aimed at the development of agents for the treatment of memory related disorders have focused on the synthesis of muscarinic ACh receptor ligands. Recently, however, an interest in the development of nAChR ligands has emerged.

Several diseases are associated with degeneration of the cholinergic system, such as senile dementia of the Alzheimer's type, vascular dementia and cognitive impairment due to the organic brain damage disease related directly to alcoholism. Indeed, several CNS disorders can be attributed to a cholinergic deficiency, a dopaminergic deficiency, an adrenergic deficiency or a serotonergic deficiency. Alzheimer's disease is characterized by a profound loss of memory and cognitive functions caused by a severe depletion of cholinergic neurons, i.e., neurons that release acetylcholine. A reduction in the number of nAChRs are also observed with the progression of Alzheimer's disease (Whitehouse P J et al. (1986) Nicotinic acetylcholine binding sites in Alzheimer's disease. Brain Research 371(1):146-151). It is predicted that treatment of Alzheimer patients with nAChR ligands will not only improve the memory of patients but in addition act to keep these neurons alive.

However degeneration of the cholinergic system is not limited to individuals suffering from, for example, Alzheimer's disease but is also seen in healthy aged adults and rats. Therefore it is suggested that the cholinergic system is involved and partly responsible for the memory disturbances seen in aged animals and humans. Nicotinic receptor ligand may therefore be useful in the treatment of Alzheimer's disease, memory loss, memory dysfunction, AIDS-dementia, senile dementia or neurodegenerative disorders.

Parkinson's disease appears to involve degeneration of dopaminergic neurons. One symptom of the disease has been observed to be loss of nAChRs associated with the dopaminergic neurons and possibly interfering with the process of release of dopamine. As sustained nicotine administration increases the number of receptors present, administration of nAChR ligands may ameliorate the symptoms of Parkinson's disease. Other condition or disorders or disease ascribed to deficiencies in the dopaminergic system is: drug addiction, depression, obesity and narcolepsy.

Tourette's syndrome is a neuropsychiatric disorder involving a range of neurological and behavioral symptoms. It is believed that neurotransmitter dysfunction is involved though the pathophysiology is still unknown and that nicotine will be beneficial in the treatment of the disease (Devor et. al. The Lancet, vol. 8670 p. 1046, 1989).

Schizophrenia is a severe psychiatric illness. Neuroleptic compounds have been used in the treatment of the disease; the effect of the compounds is believed to be based on interactions in the dopaminergic system. Nicotine is proposed to be effective in the treatment of schizophrenia (Merriam et. al. Psychiatr. Annals, Vol. 23, p. 171-178, 1993 and Adler et. al. Biol. Psychiatry, Vol. 32, p. 607-616, 1992.)

Nicotine has been reported to have en effect on neurotransmitter release in several systems. Release of acetylcholine and dopamine by neurons upon administration of nicotine has been reported (J. Neurochem. vol. 43, 1593-1598, 1984) and release of norepinephrine by Hall et. al. (Biochem. Pharmacol. vol. 21, 1829-1838, 1972), release of serotonin by Hery et. al. (Arch. Int. Pharmacodyn. Ther. vol. 296. p. 91-97, 1977). and release of glutamate by Toth et. al (Neurochem. Res. vol. 17, p. 265-271, 1992) have also been reported.

The serotonin system and dysfunction's of the serotonergic system is believed to be involved in diseases or conditions or disorders like: anxiety, depression, eating disorders, obsessive compulsive disorder, panic disorders, chemical substance abuse, alcoholism, pain, memory deficits and anxiety, pseudodementia, Ganser's syndrome, migraine pain, bulimia, obesity, pre-menstrual syndrome or late luteal phase syndrome, tobacco abuse, post-traumatic syndrome, social phobia, chronic fatigue syndrome, premature ejaculation, erectile difficulty, anorexia nervosa, disorders of sleep, autism, mutism and trichotillomania.

Nicotine improves concentration and task performance. Therefore compounds exhibiting nAChR modulating properties will be likely to be useful compounds in the treatment of learning deficit, cognition deficit, attention deficit, attention deficit hyperactivity disorder and dyslexia.

Tobacco use and especially cigarette smoking is recognized as a serious health problem. However nicotine withdrawal symptoms associated with smoking cessation makes it difficult to break this habit. Withdrawal symptoms include anger, anxiety, difficulties in concentrating, restlessness, decreased heart rate and increased appetite and weight gain. Nicotine itself has shown to ease the withdrawal symptoms.

Withdrawal from addictive substances, such as opiates, benzodiazepines, ethanol, tobacco or nicotine, is in general a traumatic experience characterized by anxiety and frustration. Nicotine has been found to be effective in reducing anger, irritability, frustration and feelings of tension without causing general response depression, drowsiness or sedation and compounds targeting nAChRs is likely to have same effects.

Mild to moderate pain is typically treatable with NSAIDs (non-steroidal anti-inflammatory drugs), while opiates are used preferentially for moderate to severe pain. The opiates have some well-known side-effects, including chemical dependence and abuse potential, as well as a depressive effect on the respiratory and gastrointestinal system. There exists, therefore, a pressing need for analgesic compounds that do not exhibit these side effects and which can relieve mild, moderate and severe pain of acute, chronic or recurrent character, as well as migraine pain, postoperative pain, and phantom limb pain.

Epibatidine, a compound isolated from the skin of a poison frog, is a very potent analgesic with an approximate potency of 200 times that of morphine. The analgesic effect is not affected by naloxone, which is an indication of a negligible affinity for the opiate receptors. Epibatidine is an nAChR agonist and it is therefore very likely, that compounds possessing this receptor modulating character will also show a strong analgesic response. It is well known that nicotine has an effect on appetite and it is predicted that ligands at the nicotine ACh receptor may be useful as appetite suppressants in the treatment of obesity and eating disorders.

In addition to epibatidine, various heterocyclic 2-pyrrolidinyloxy-substituted compounds with analgesic and hypotensive activities have been disclosed by Scheffler et al. (U.S. Pat. No. 4,643,995) and Tomioka et al. (Chem. Pharm. Bull, 38:2133-5, 1990).

Certain other 2-pyridyloxy-substituted compounds are disclosed inter alia by Engel et al. in U.S. Pat. No. 4,946,836 as having analgesic activity.

Various other compounds having a pyrrolidine or azetidine moiety substituted at the 3-position with a heterocycloxy group have also been disclosed (see, for example, U.S. Pat. No. 4,592,866 to A. D. Cale; U.S. Pat. No. 4,705,853 to A. D. Cale; U.S. Pat. No. 4,956,359 to Taylor et al.; U.S. Pat. No. 5,037,841 to Schoehe et al.; US Pat. App. Pub. No. 2008/0132486 to Kozikowski et al; PCT Patent App. Pub. No. WO 2008/011484 A2 to Xiao et al; and European Pat. App. No. EP296560 A2 to Sugimoto et al).

The cholinergic receptors play an important role in the functioning of muscles, organs and generally in the central nervous system. There are also complex interactions between cholinergic receptors and the function of receptors of other neurotransmitters such as dopamine, serotonin and noradrenaline.

SUMMARY

One aspect of the invention relates to compounds which are nAChR ligands (i.e., nicotinic ligands) and which have the potential to exhibit nicotinic pharmacology, preferentially without the side effects associated with nicotine itself. Additionally, the compounds are expected to have the potential as modulators of neurotransmitter secretion and suppress symptoms associated with concentrations of neurotransmitters.

In part, the present invention relates to a compound of formula I:

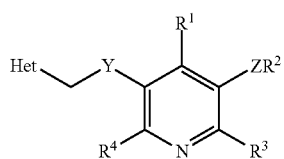

or a pharmaceutically-acceptable tautomer, salt, solvate and/or ester thereof, wherein Y is O, S or N($R^C$);
$R^C$ is hydrogen, alkyl or aralkyloxycarbonyl;
Het is optionally-substituted heterocyclyl;
Z is optionally-substituted arylene or optionally-substituted heteroarylene;
$R^1$, $R^3$ and $R^4$ are independently selected from the group consisting of hydrogen, alkyl, alkenyl, alkynyl, halo, hydroxy, alkoxy, amino, alkylamino, dialkylamino, cyano, nitro, formyl, carboxy, alkyloxycarbonyl, aminocarbonyl, alkylaminocarbonyl, dialkylaminocarbonyl, haloalkyl, haloalkoxy, haloalkylamino, di(haloalkyl)amino, silyl and silyloxy, wherein said alkyl, alkenyl and alkynyl may be substituted with one, two, three or four substituents selected from the group consisting of hydroxy, alkoxy, amino, alkylamino, dialkylamino, cyano, nitro, formyl, carboxy, alkyloxycarbonyl, aminocarbonyl, alkylaminocarbonyl, dialkylaminocarbonyl, haloalkyl, haloalkoxy, haloalkylamino, di(haloalkyl)amino, silyl and silyloxy;

$R^2$ is

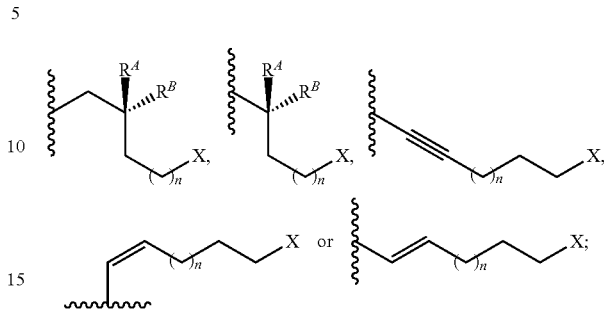

$R^A$ is hydrogen or alkyl;
$R^B$ is hydrogen or alkyl;
n is 0, 1, 2, 3 or 4; and
X is hydrogen, halo, hydroxyl, alkyloxy, trifluoromethyl or alkyl.

In another embodiment, the present invention relates to a method of modulating a nicotine ACh receptor in a mammal comprising administering to the mammal a nicotinic desensitizer of formula I, or a pharmaceutically-acceptable tautomer, salt, solvate and/or ester thereof.

In another embodiment, the present invention relates to a method of treating of one or more conditions or diseases associated aging, addiction, pain, obesity, schizophrenia, epilepsy, mania and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, amyotrophic lateral sclerosis, inflammation, stoke and spinal-cord injury, inflammation, inflammatory skin conditions, Chron's disease, inflammatory bowel disease, ulcerative colitis, diarrhea, endocrine disorders, thyrotoxicosis, pheochromocytoma, hypertension, and cough, comprising administering a therapeutically effective amount of a nicotinic desensitizer of formula I, or a pharmaceutically-acceptable tautomer, salt, solvate and/or ester thereof.

In another embodiment, the present invention relates to a method of weight control, comprising administering a therapeutically effective amount of a nicotinic desensitizer of formula I, or a pharmaceutically-acceptable tautomer, salt, solvate and/or ester thereof.

In another embodiment, the present invention relates to a method for treating combination addictions, such as nicotine and alcohol, or nicotine and cocaine, comprising administering a therapeutically effective amount of a nicotinic desensitizer of formula I, or a pharmaceutically-acceptable tautomer, salt, solvate and/or ester thereof.

As explained herein in greater detail, the invention will readily enable the design and implementation of trials in warm-blooded animals, including humans and mammals, necessary for easily determining or tailoring the form and dose for any composition of the present invention.

These embodiments of the present invention, other embodiments, and their features and characteristics, will be apparent from the description, drawings and claims that follow.

BRIEF DESCRIPTION OF THE FIGURES

FIG. 2 depicts predicted values for clog P and PSA.

FIG. 7 depicts the use of a Pd-mediated Negishi coupling to prepare a triazole compound of the invention.

FIG. 8 depicts representative series of organozinc reagents that could be used for the Negishi reaction shown in FIG. 7.

DETAILED DESCRIPTION

Figure 1:
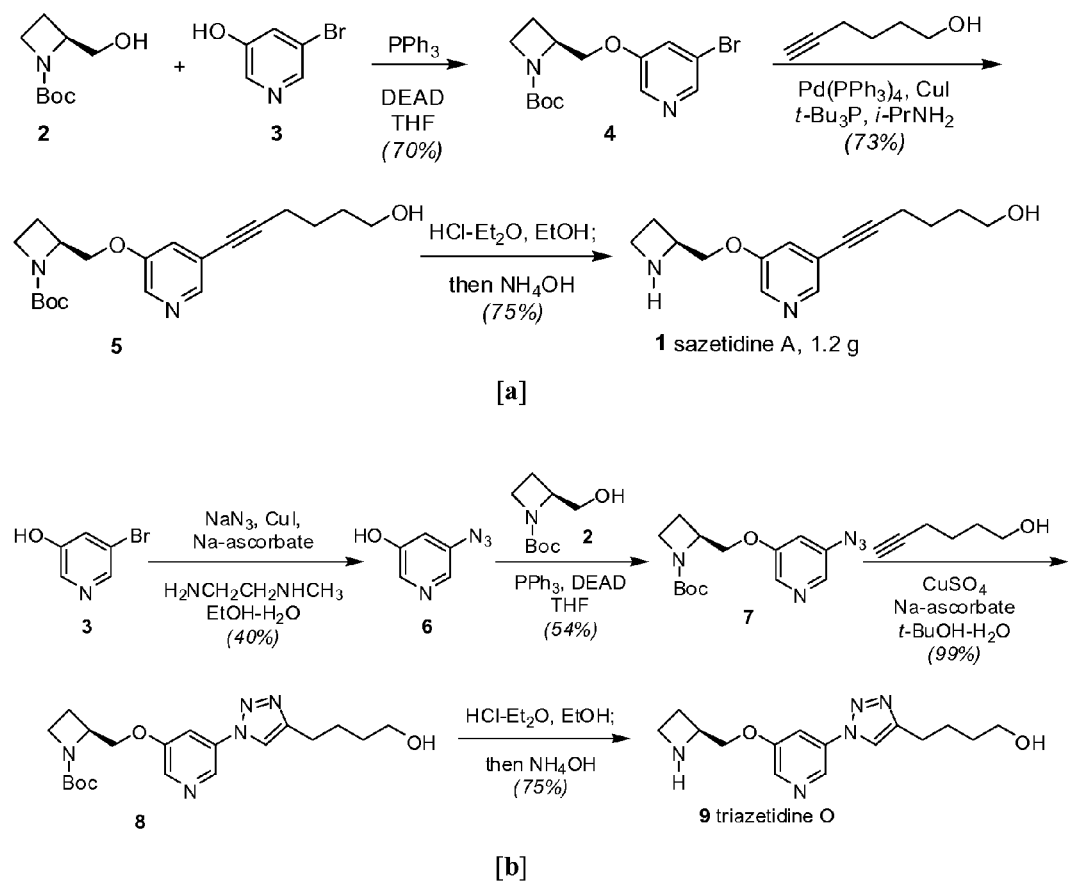
FIG. 1 depicts [a] a route for the synthesis of sazetidine A; [b] a route for the synthesis of triazetidine O (a triazole analog of sazetidine A); and [c] the effect sazetidine A and triazetidine O on nitcotinic receptors; $IC_{50}$ values shown are the results of desensitizer tests.

The effect of drug abuse in the US is devastating. Abuse of illicit drugs and alcohol resulted in over 102,000 deaths in the year 2000. Abuse of tobacco products alone is attributed to 435,000 deaths in that same year. The combined medical, economical, criminal, and societal impact of alcohol, nicotine, and illicit drug abuse is estimated to cost upwards of half-a-trillion dollars per year in the US. Drug addiction has generally been viewed primarily as a social problem, not a health problem. This has resulted in a disparity of medical approaches available to the physician for treating chemical dependency. Drug addiction is now known to be a chronic brain disease. There is no reliable cure for drug addiction, and the rate of relapse can be as high as 60%, which correlates with other chronic diseases. Therefore, an urgent need exists to address directly this dearth of treatment options by developing novel small molecule agents (such as nicotinic desensitizers) for the treatment of drug abuse.

Addiction

Drugs of abuse have differing mechanisms of action, but share a common pathway toward physical dependency. The mesolimbic dopamine pathway is widely accepted as a central pathway in producing the rewarding effects of addictive drugs. This pathway includes the dopaminergic neurons in the ventral tegmental area (VTA) of the midbrain and their targets in the limbic forebrain, especially the nucleus accumbens (NAc). All drugs of abuse, regardless of their mechanisms of actions, converge on the VTA-NAc pathway. Acute exposure to addictive drugs results in the elevation of dopamine levels, a reward signaling event, which promotes repeated drug intake. Addiction is then reinforced by the drugs producing a negative emotional symptom when the drug is removed, developing a period of sensitization, and associative learning toward drug-related environmental cues.

The nAChRs may be an important target for the treatment of multiple addictions, not just nicotine. Activation of the central nAChRs has been shown to also mediate the reinforcing effects of other drugs of abuse including alcohol and cocaine. Behavior sensitization induced by nicotine, amphetamine, or cocaine was shown to be associated with an increase in electrically evoked release of [3H]dopamine in nucleus accumbens slices, suggesting a related pathway for these three different drugs.

The nAChR and Nicotinic Ligands

The nAChR α4β2 subtype is implicated in the addictive effects of nicotine. In general, the nAChRs are integral membrane proteins of approximately 290 kDa and members of the Cys-loop superfamily of receptor-coupled ion channels. These receptors are ligand-gated ion channels that are permeable to cations, particularly Na+, K+, and Ca++. The neuronal nAChRs are pentameric membrane proteins composed of five subunits. To date, nine α subunits (α2-α10) and three β subunits (β2-β4) have been found in vertebrates. Different combinations of these α and β subunits define nAChR subtypes. Although the theoretical number of potential subtypes is very large, a much smaller number of native nAChR subtypes represent the majority of neuronal nAChRs, including two heteromeric subtypes, α4β2 and α3β4, and one homomeric subtype, α7. In most areas of mammalian brain, the target subtype α4β2 represents the predominant population of nAChRs.

The nAChRs are allosteric proteins that respond to the action of ACh at the binding site by changing the status of the channel gate to carry out the function of the nAChR. The receptors have at least three discrete conformational states: a resting state (closed), an open state (opened) and a desensitized state (closed). A particular nicotinic ligand, such as ACh, has a certain affinity for each of the three states. In the absence of bound ligand, nAChRs fluctuate among all three conformational states, but most of the time they are in the resting state. The binding of a ligand to a certain state of the receptor increases the probability of the receptor to be in that state. For example, an agonist binds with a reasonably high affinity to the open state of a receptor, and thus increases the probability of it being in the open (active) conformational state. For a population of receptors, the overall initial effect of an agonist is to shift a certain subpopulation of receptors from the resting state to the open state. In the open state, cations flow through the channel. However, agonists have an even higher affinity for the desensitized state of the receptor; therefore, the eventual effect of an agonist is to "drive" the receptor population from the resting and open states to the desensitized state, in which receptors remain closed. The kinetic rates for transitions between states vary greatly among different nAChR subtypes, which contribute to the great functional diversity of neuronal nAChRs.

In addition to ACh and nicotine, many other natural products and synthetic compounds act on nAChRs (Cassels B K, Bermudez I, Dajas F, Abin-Carriquiry J A and Wonnacott S (2005) From ligand design to therapeutic efficacy: the challenge for nicotinic receptor research. Drug Discov Today 10(23-24):1657-1665; Daly J W (2005) Nicotinic agonists, antagonists, and modulators from natural sources. Cell Mol Neurobiol 25(3-4):513-552; Jensen A A, Frolund B, Liljefors T and Krogsgaard-Larsen P (2005) Neuronal nicotinic acetylcholine receptors: structural revelations, target identifications, and therapeutic inspirations. Journal of medicinal chemistry 48(15):4705-4745; Paterson D and Nordberg A (2000) Neuronal nicotinic receptors in the human brain. Progress in neurobiology 61(1):75-111). Nicotinic ligands belong to the following four major classes, defined classically, according to their actions.

(1) Agonists. Nicotinic agonists, such as ACh or nicotine, activate nAChRs leading to the opening of their channels, which allows cations to cross the membrane; but prolonged presence of agonists desensitizes the receptors. The actions can be explained by the three-state model, as described above. Agonists have low binding affinity at the resting state of nAChRs, higher affinity at the open state, and highest binding affinity at the desensitized state. After an agonist binds, the transition from the resting state to the open state is fast, but the transition from open state to desensitized state is slow. Therefore, agonists can activate receptors to open their channels initially but if present for an extended period, agonists desensitize receptors to close the channels.

(2) Competitive Antagonists. A competitive antagonist, such as dihydro-β-erythroidine (DHβE), does not activate nAChRs but prevents agonists from activating the receptor by occupying the ACh binding site. A possible mechanism is that competitive antagonists have higher binding affinity at the resting state of receptors than at the open state; therefore, they do not increase the probability of the open state but can prevent agonists from binding to the ACh site.

(3) Noncompetitive Antagonists. A noncompetitive antagonist, such as mecamylamine, does not activate nAChRs but prevents an agonist from activating nAChRs by binding to a site different from the ACh site. For example, the binding site for mecamylamine is in the central pore of the receptors, and so it blocks the pathway for ions, preventing the functional activity of an agonist.

(4) Allosteric Modulators. An allosteric modulator, such as progesterone (Buisson and Bertrand, 1998), does not bind to the acetylcholine binding site (orthosteric site) but modulates nAChR signaling through its binding to an allosteric site. There are positive and negative allosteric modulators of nAChRs and some of them show selectivity among nAChR subtypes.

Of the major nAChR subtypes, the α4β2 subtype stands out not only because of its prevalence in most of the brain, but also because it is increased by chronic administration of nicotine in rats and mice (Flores C M, Rogers S W, Pabreza L A, Wolfe B B and Kellar K J (1992) A subtype of nicotinic cholinergic receptor in rat brain is composed of alpha 4 and beta 2 subunits and is up-regulated by chronic nicotine treatment. Molecular pharmacology 41(1):31-37; Marks M J, Burch J B and Collins A C (1983) Effects of chronic nicotine infusion on tolerance development and nicotinic receptors. The Journal of pharmacology and experimental therapeutics 226(3):817-825; Schwartz R D and Kellar K J (1983) Nicotinic cholinergic receptor binding sites in the brain: regulation in vivo. Science (New York, N.Y. 220(4593):214-216) and in human brain from smokers (Benwell M E, Balfour D J and Anderson J M (1988) Evidence that tobacco smoking increases the density of (−)-[3H]nicotine binding sites in human brain. Journal of neurochemistry 50(4):1243-1247; Breese C R, Marks M J, Logel J, Adams C E, Sullivan B, Collins A C and Leonard S (1997) Effect of smoking history on [3H]nicotine binding in human postmortem brain. The Journal of pharmacology and experimental therapeutics 282 (1):7-13; Perry D C, Davila-Garcia M I, Stockmeier C A and Kellar K J (1999) Increased nicotinic receptors in brains from smokers: membrane binding and autoradiography studies. The Journal of pharmacology and experimental therapeutics 289(3):1545-1552). Moreover, recent in vivo studies that imaged brain α4β2 nAChRs in human smokers indicate that these receptors are virtually saturated by the nicotine taken in during the smoking of a single cigarette (Brody A L, Mandelkern M A, London E D, Olmstead R E, Farahi J, Scheibal D, Jou J, Allen V, Tiongson E, Chefer S I, Koren A O and Mukhin A G (2006) Cigarette smoking saturates brain alpha 4 beta 2 nicotinic acetylcholine receptors. Arch Gen Psychiatry 63(8):907-915). Therefore, it is likely that most of the α4β2 nAChRs in a smoker's brain are in a state of desensitization during the time the addicted individual is awake and smoking at a typical rate. In fact, as the nicotine concentration drops and the increased numbers of desensitized receptors begin to recover function, the resumption of endogenous acetylcholine signaling through even a relatively small percentage of these receptors, may provide the critical neurophysiological cues for the individual to smoke his/her next cigarette and thus silence those cues by once again desensitizing the receptors. Under this scenario, an addicted individual smokes not to achieve a direct positive reward from nicotine, but to prevent the negative effects that ensue when the increased number of α4β2 nAChRs return to functional status (Xiao Y, Fan H, Musachio J L, Wei Z L, Chellappan S K, Kozikowski A P and Kellar K J (2006) Sazetidine-A, a novel ligand that desensitizes alpha4beta2 nicotinic acetylcholine receptors without activating them. Molecular Pharmacology 70(4):1454-1460).

Sazetidine A, a Selective α4β2-Desensitizer

Sazetidine-A (Saz-A) is a new, highly selective α4β2 nAChR ligand. In radioligand binding assays, Saz-A had very high affinity for α4β2 nAChRs and, more importantly, it was greater than 10,000-fold and 3,500-fold selective compared to its affinity at α3β4 and α7 nAChRs, respectively. Despite its high affinity for α4β2 nAChRs in radioligand binding studies, functional measurements detected only low agonist activity when Saz-A was added alone. Furthermore, no typical antagonist activity at these α4β2 receptors were detected when added simultaneously with an agonist, such as nicotine. However, when it was preincubated for 10 min with these cells Saz-A potently ($EC_{50}$=26 nM) and completely desensitized the α4β2 nAChRs (Xiao Y, Fan H, Musachio J L, Wei Z L, Chellappan S K, Kozikowski A P and Kellar K J (2006) Sazetidine-A, a novel ligand that desensitizes alpha4beta2 nicotinic acetylcholine receptors without activating them. Molecular Pharmacology 70(4):1454-1460). Consistent with its high selectivity for α4β2 receptors in binding studies, Saz-A at concentrations up to 10 µM had no effect on the function of α3β4 nAChRs, even after preincubation (Xiao Y, Fan H, Musachio J L, Wei Z L, Chellappan S K, Kozikowski A P and Kellar K J (2006) Sazetidine-A, a novel ligand that desensitizes alpha4beta2 nicotinic acetylcholine receptors without activating them. Molecular Pharmacology 70(4): 1454-1460).

Saz-A is an excellent lead molecule for drug discovery and it shows important properties in several animal models (Cucchiaro G, Xiao Y, Gonzalez-Sulser A and Kellar K J (2008) Analgesic effects of Sazetidine-A, a new nicotinic cholinergic drug. Anesthesiology 109(3):512-519; Levin E D, Hampton D, Xiao Y and Kellar K J (2007) Sazetidine-A, a nicotinic desensitizing agent, decrease nicotine self-administration in rats. Biochemical pharmacology 74(8):SMA-43; Xiao Y, Woolverton W L, Sahibzada N, Yasuda R P and Kellar K J (2007) Pharmacological properties of sazetidine-A, a desensitizer of α4β2 nicotinic acetylcholine receptors, in Society for Neuroscience 37th Annual Meeting, Abstracts (#574.6), San Diego), which indicate its potential use in blocking pain, aiding smoking cessation and treating other conditions. In certain embodiments, compounds of the present invention may also be used in blocking pain, aiding smoking cessation and treating other conditions.

Selected Compounds of the Invention

In part, the present invention relates to a compound of formula I:

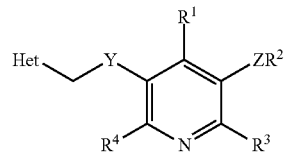

or a pharmaceutically-acceptable tautomer, salt, solvate and/or ester thereof, wherein Y is O, S or N($R^C$);

$R^C$ is hydrogen, alkyl or aralkyloxycarbonyl;

Het is optionally-substituted heterocyclyl;

Z is optionally-substituted arylene or optionally-substituted heteroarylene;

$R^1$, $R^3$ and $R^4$ are independently selected from the group consisting of hydrogen, alkyl, alkenyl, alkynyl, halo, hydroxy, alkoxy, amino, alkylamino, dialkylamino, cyano, nitro, formyl, carboxy, alkyloxycarbonyl, aminocarbonyl, alkylaminocarbonyl, dialkylaminocarbonyl, haloalkyl, haloalkoxy, haloalkylamino, di(haloalkyl)amino, silyl and silyloxy, wherein said alkyl, alkenyl and alkynyl may be substituted with one, two, three or four substituents selected from the group consisting of hydroxy, alkoxy, amino, alkylamino, dialkylamino, cyano, nitro, formyl, carboxy, alkyloxycarbonyl, aminocarbonyl, alkylaminocarbonyl, dialkylaminocarbonyl, haloalkyl, haloalkoxy, haloalkylamino, di(haloalkyl)amino, silyl and silyloxy;

$R^2$ is

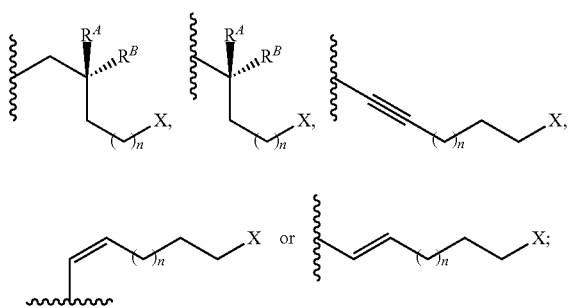

$R^A$ is hydrogen or alkyl;

$R^B$ is hydrogen or alkyl;

n is 0, 1, 2, 3 or 4; and

X is hydrogen, halo, hydroxyl, alkyloxy, trifluoromethyl or alkyl.

In certain embodiments, the present invention relates to any one of the aforementioned compounds, wherein Y is O.

In certain embodiments, the present invention relates to any one of the aforementioned compounds, wherein Y is S.

In certain embodiments, the present invention relates to any one of the aforementioned compounds, wherein Y is N($R^C$). In certain embodiments, the present invention relates to any one of the aforementioned compounds, wherein Y is N($R^C$); and $R^C$ is hydrogen. In certain embodiments, the present invention relates to any one of the aforementioned compounds, wherein Y is N($R^C$); and $R^C$ is alkyl. In certain embodiments, the present invention relates to any one of the aforementioned compounds, wherein Y is N($R^C$); and $R^C$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$ or —$CH(CH_2CH_3)_2$.

In certain embodiments, the present invention relates to any one of the aforementioned compounds, wherein Het is an optionally-substituted azetidenyl or an optionally-substituted pyrrolidinyl. In certain embodiments, the present invention relates to any one of the aforementioned compounds, wherein Het is

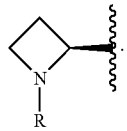

In certain embodiments, the present invention relates to any one of the aforementioned compounds, wherein Het is

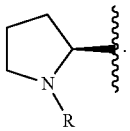

In certain embodiments, the present invention relates to any one of the aforementioned compounds, wherein R is hydrogen. In certain embodiments, the present invention relates to any one of the aforementioned compounds, wherein R is alkyl. In certain embodiments, the present invention relates to any one of the aforementioned compounds, wherein R is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$ or —$CH(CH_2CH_3)_2$. In certain embodiments, the present invention relates to any one of the aforementioned compounds, wherein R is aralkyloxycarbonyl. In certain embodiments, the present invention relates to any one of the aforementioned compounds, wherein R is benzyloxycarbonyl (Boc).

In certain embodiments, the present invention relates to any one of the aforementioned compounds, wherein Z is

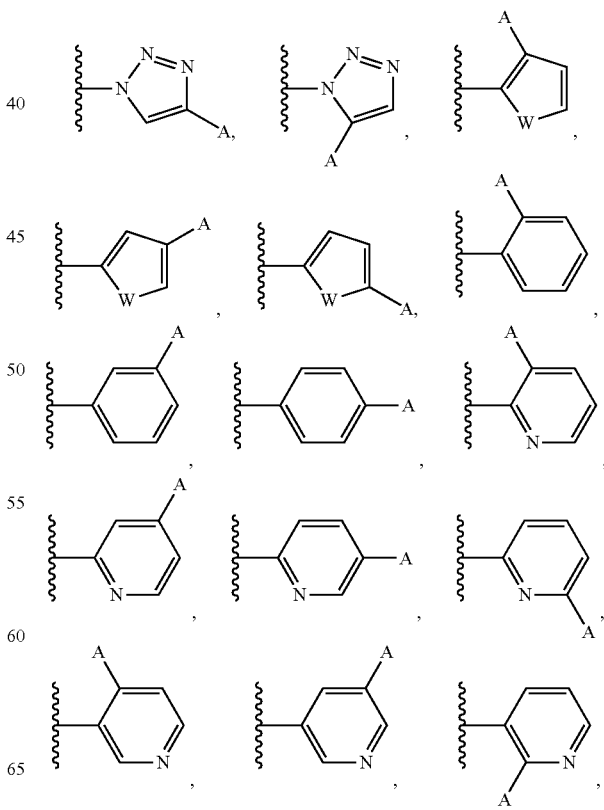

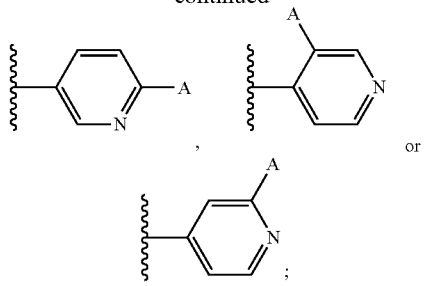

A is a bond to $R^2$; W is O, S or $N(R^D)$; and $R^D$ is hydrogen, alkyl or aralkyloxycarbonyl.

In certain embodiments, the present invention relates to any one of the aforementioned compounds, wherein Z is

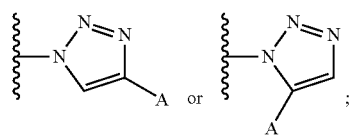

and A is a bond to $R^2$.

In certain embodiments, the present invention relates to any one of the aforementioned compounds, wherein Z is

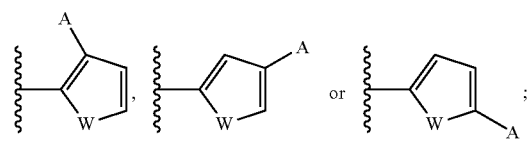

A is a bond to $R^2$; W is O, S or $N(R^D)$; and $R^D$ is hydrogen, alkyl or aralkyloxycarbonyl. In certain embodiments, the present invention relates to any one of the aforementioned compounds, wherein W is O. In certain embodiments, the present invention relates to any one of the aforementioned compounds, wherein W is S. In certain embodiments, the present invention relates to any one of the aforementioned compounds, wherein W is $N(R^D)$. In certain embodiments, the present invention relates to any one of the aforementioned compounds, wherein $R^D$ is hydrogen. In certain embodiments, the present invention relates to any one of the aforementioned compounds, wherein $R^D$ is alkyl. In certain embodiments, the present invention relates to any one of the aforementioned compounds, wherein $R^D$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$ or —$CH(CH_2CH_3)_2$.

In certain embodiments, the present invention relates to any one of the aforementioned compounds, wherein Z is

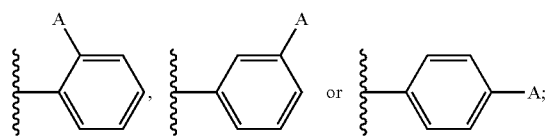

and A is a bond to $R^2$.

In certain embodiments, the present invention relates to any one of the aforementioned compounds, wherein Z is

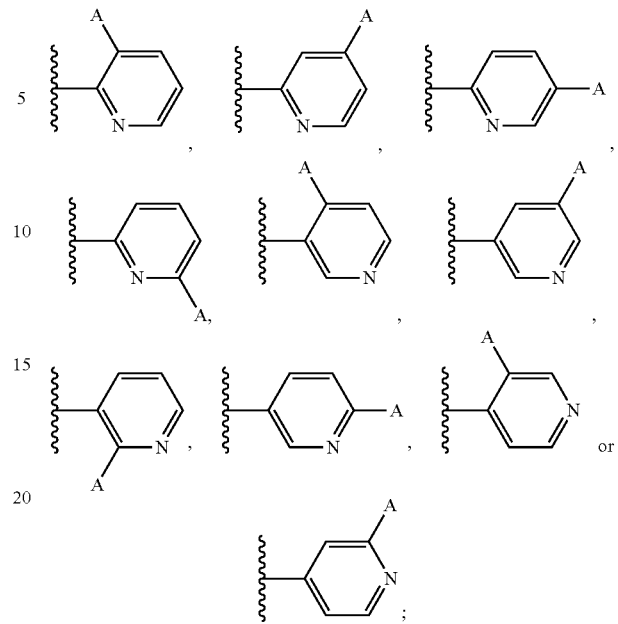

and A is a bond to $R^2$.

In certain embodiments, the present invention relates to any one of the aforementioned compounds, wherein $R^1$ is hydrogen, halo or alkyl. In certain embodiments, the present invention relates to any one of the aforementioned compounds, wherein $R^1$ is hydrogen. In certain embodiments, the present invention relates to any one of the aforementioned compounds, wherein $R^1$ is chloro. In certain embodiments, the present invention relates to any one of the aforementioned compounds, wherein $R^1$ is —$CH_3$.

In certain embodiments, the present invention relates to any one of the aforementioned compounds, wherein $R^3$ is hydrogen, halo or alkyl. In certain embodiments, the present invention relates to any one of the aforementioned compounds, wherein $R^3$ is hydrogen. In certain embodiments, the present invention relates to any one of the aforementioned compounds, wherein $R^3$ is chloro. In certain embodiments, the present invention relates to any one of the aforementioned compounds, wherein $R^3$ is —$CH_3$.

In certain embodiments, the present invention relates to any one of the aforementioned compounds, wherein $R^4$ is hydrogen, halo or alkyl. In certain embodiments, the present invention relates to any one of the aforementioned compounds, wherein $R^4$ is hydrogen. In certain embodiments, the present invention relates to any one of the aforementioned compounds, wherein $R^4$ is chloro. In certain embodiments, the present invention relates to any one of the aforementioned compounds, wherein $R^4$ is —$CH_3$.

In certain embodiments, the present invention relates to any one of the aforementioned compounds, wherein $R^2$ is

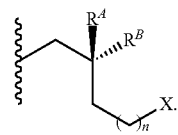

In certain embodiments, the present invention relates to any one of the aforementioned compounds, wherein $R^2$ is

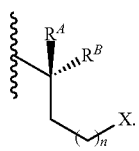

In certain embodiments, the present invention relates to any one of the aforementioned compounds, wherein $R^2$ is

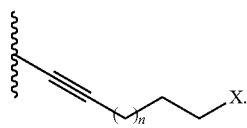

In certain embodiments, the present invention relates to any one of the aforementioned compounds, wherein $R^2$ is

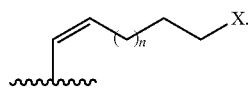

In certain embodiments, the present invention relates to any one of the aforementioned compounds, wherein $R^2$ is

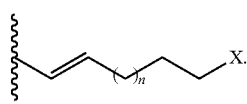

In certain embodiments, the present invention relates to any one of the aforementioned compounds, wherein n is 0. In certain embodiments, the present invention relates to any one of the aforementioned compounds, wherein n is 1. In certain embodiments, the present invention relates to any one of the aforementioned compounds, wherein n is 2. In certain embodiments, the present invention relates to any one of the aforementioned compounds, wherein n is 3. In certain embodiments, the present invention relates to any one of the aforementioned compounds, wherein n is 4.

In certain embodiments, the present invention relates to any one of the aforementioned compounds, wherein X is hydrogen. In certain embodiments, the present invention relates to any one of the aforementioned compounds, wherein X is halo. In certain embodiments, the present invention relates to any one of the aforementioned compounds, wherein X is fluoro. In certain embodiments, the present invention relates to any one of the aforementioned compounds, wherein X is hydroxy. In certain embodiments, the present invention relates to any one of the aforementioned compounds, wherein X is trifluoromethyl. In certain embodiments, the present invention relates to any one of the aforementioned compounds, wherein X is alkyl. In certain embodiments, the present invention relates to any one of the aforementioned compounds, wherein X is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$ or —$CH(CH_2CH_3)_2$.

In certain embodiments, the present invention relates to any one of the aforementioned compounds, wherein $R^A$ is hydrogen. In certain embodiments, the present invention relates to any one of the aforementioned compounds, wherein $R^A$ is alkyl. In certain embodiments, the present invention relates to any one of the aforementioned compounds, wherein $R^A$ is —$CH_2$ or —$CH_2CH_3$.

In certain embodiments, the present invention relates to any one of the aforementioned compounds, wherein $R^B$ is hydrogen. In certain embodiments, the present invention relates to any one of the aforementioned compounds, wherein $R^B$ is alkyl. In certain embodiments, the present invention relates to any one of the aforementioned compounds, wherein $R^B$ is —$CH_2$ or —$CH_2CH_3$.

In certain embodiments, the present invention relates to a compound of formula I selected from the group consisting of:

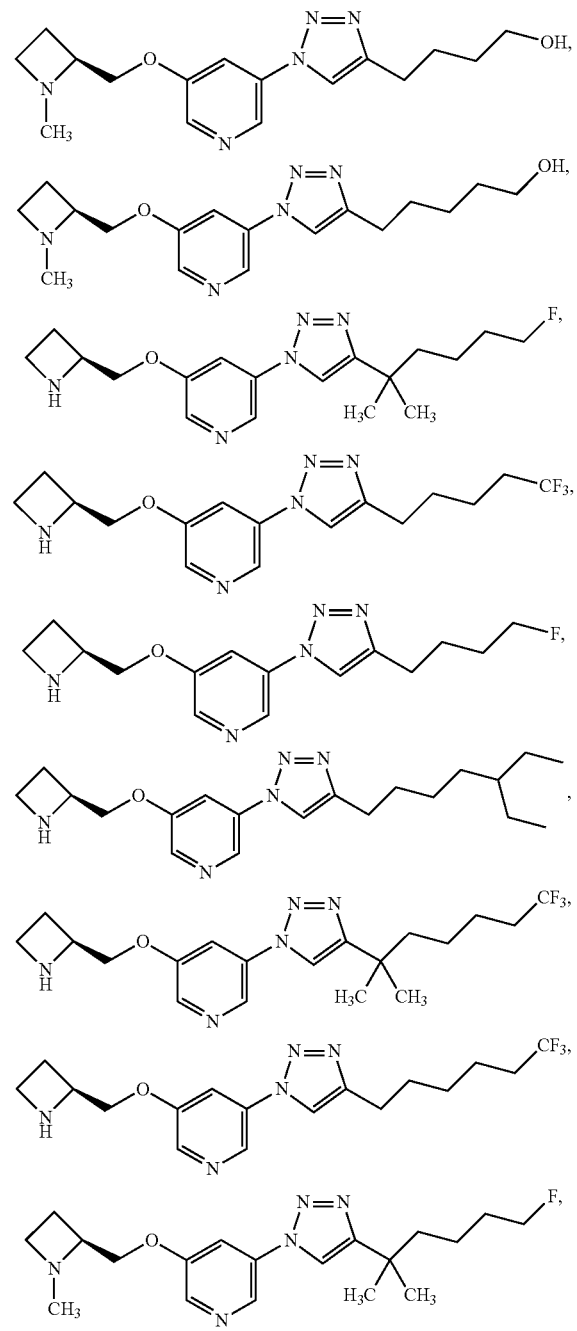

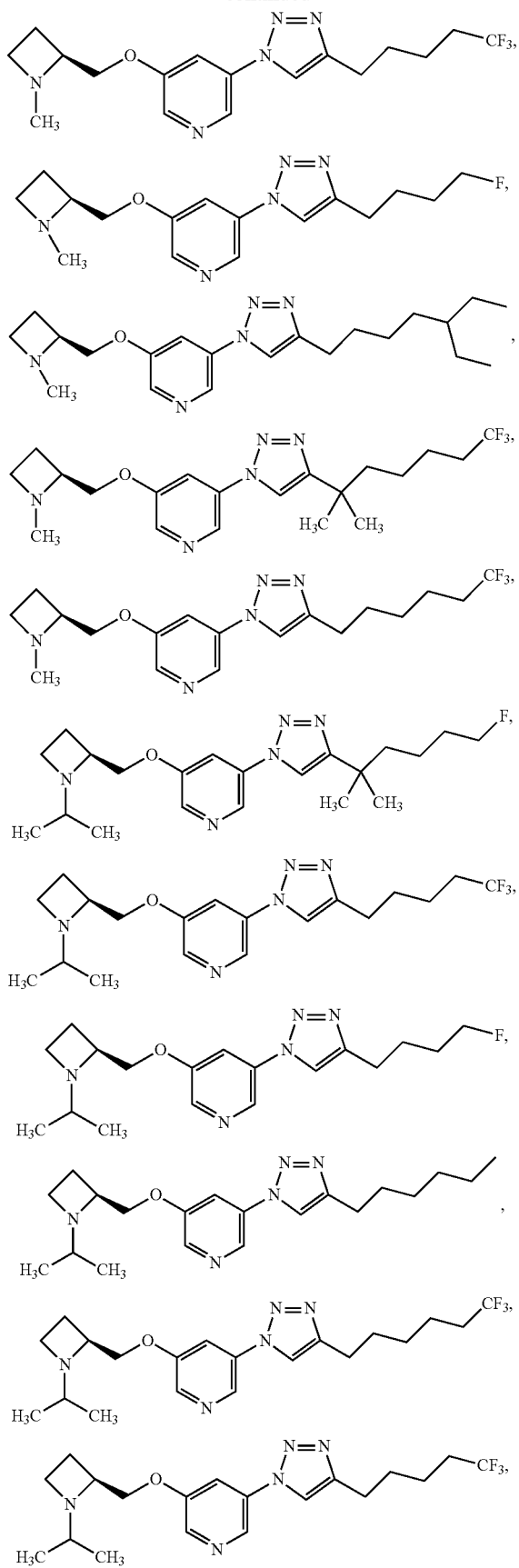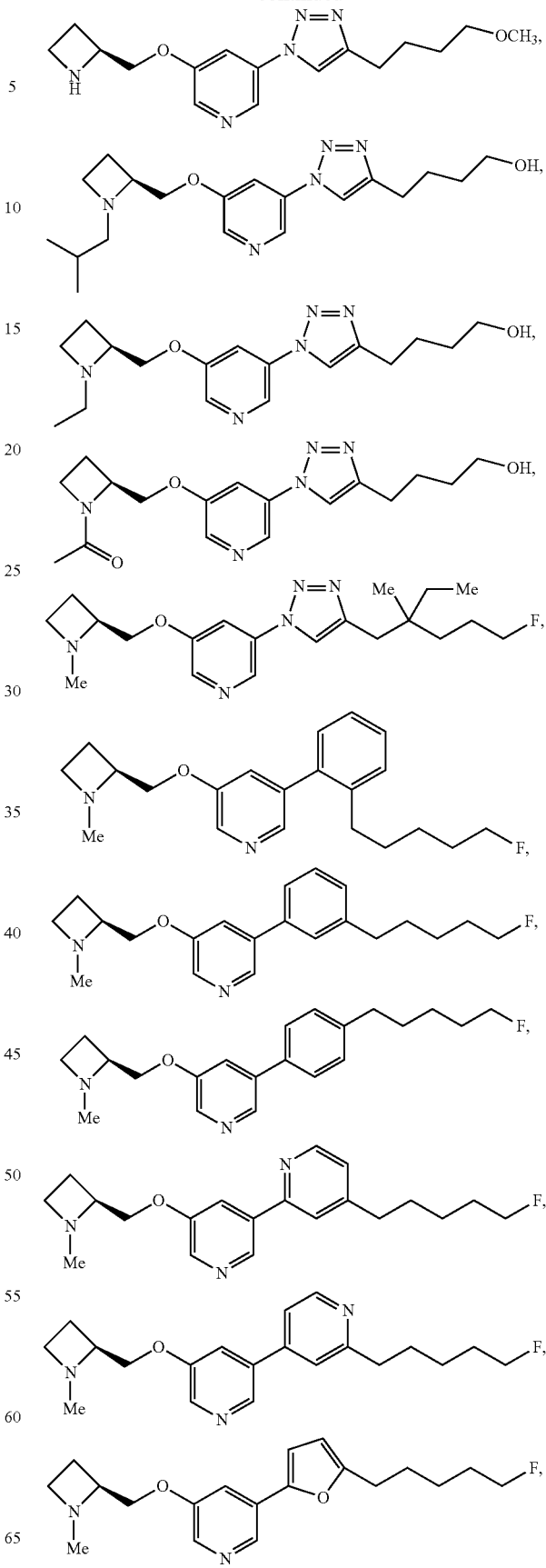

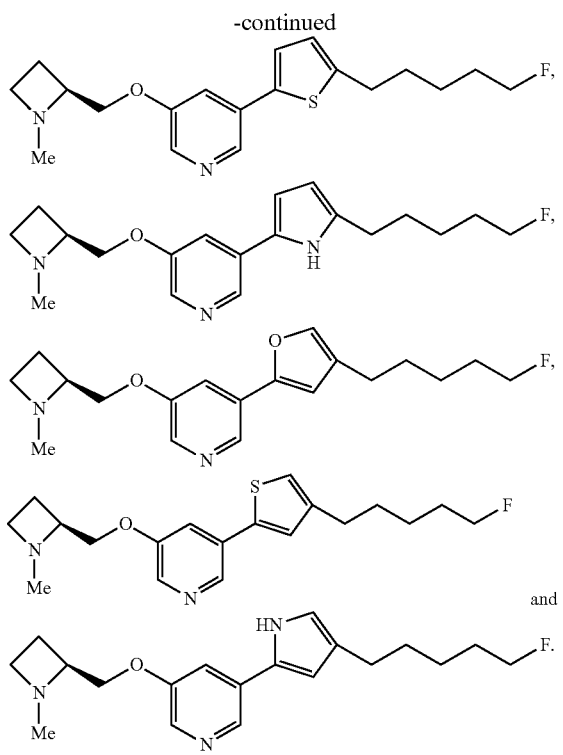

In another embodiment, the present invention relates to a pharmaceutical composition comprising a compound of formula I, or a pharmaceutically-acceptable tautomer, salt, solvate and/or ester thereof, and a pharmaceutically acceptable excipient.

In cases in which the compounds of formula I, or a pharmaceutically-acceptable tautomer, salt, solvate and/or ester thereof, have unsaturated carbon-carbon double bonds, both the cis (Z) and trans (E) isomers are within the scope of this invention. In cases wherein the compounds may exist in tautomeric forms, such as keto-enol tautomers, such as

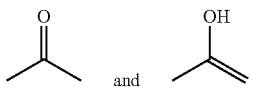

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included in the nicotine AChR ligand compounds of the present invention are prodrugs of the compounds of formula I, or a pharmaceutically-acceptable tautomer, salt, solvate and/or ester thereof. Prodrugs are considered to be any covalently bonded carriers which release the active parent drug in vivo.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

In another embodiment, the present invention relates to a compound of formula I, or a pharmaceutically-acceptable tautomer, salt, solvate and/or ester thereof, which is a nicotinic desensitizer.

In a further embodiment, the nicotinic desensitizer of formula I, or a pharmaceutically-acceptable tautomer, salt, solvate and/or ester thereof, has an $IC_{50}$ less than 1 μM in an assay based on a mammalian nicotine ACh receptor. In a further embodiment, the nicotinic desensitizer of formula I, or a pharmaceutically-acceptable tautomer, salt, solvate and/or ester thereof, has an $IC_{50}$ less than 100 nM in an assay based on a mammalian nicotine ACh receptor. In a further embodiment, the nicotinic desensitizer of formula I, or a pharmaceutically-acceptable tautomer, salt, solvate and/or ester thereof, has an $IC_{50}$ less than 10 nM in an assay based on a mammalian nicotine ACh receptor. In a further embodiment, the nicotinic desensitizer of formula I, or a pharmaceutically-acceptable tautomer, salt, solvate and/or ester thereof, has an $IC_{50}$ less than 1 nM in an assay based on a mammalian nicotine ACh receptor.

In another embodiment, the present invention relates to a nicotinic desensitizer of formula I, or a pharmaceutically-acceptable tautomer, salt, solvate and/or ester thereof, which has an $EC_{50}$ less than 1 μM. In a further embodiment the nicotinic desensitizer of formula I, or a pharmaceutically-acceptable tautomer, salt, solvate and/or ester thereof, has an $EC_{50}$ less than 100 nM in an assay based on a mammalian nicotine ACh receptor. In a further embodiment, the nicotinic desensitizer of formula I, or a pharmaceutically-acceptable tautomer, salt, solvate and/or ester thereof, has an $EC_{50}$ less than 10 nM in an assay based on a mammalian nicotine ACh receptor.

In one embodiment, the nicotinic desensitizer of formula I, or a pharmaceutically-acceptable tautomer, salt, solvate and/or ester thereof is a compound wherein (1) the binding affinity ($K_d$ or Kj) of which to a nAChR subtype is less than about 1,000 nM; (2) the agonist activity ($E_{max}$) of which for the nAChR subtype is less than about 10% of the $E_{max}$ of a typical nicotinic agonist for the nAChR subtype; and (3) the inhibition of which to receptor activation of the nAChR subtype by the typical nicotinic agonist ($IC_{50(A)}$) is more than about 1,000 nM when the compound is applied to the nAChR subtype simultaneously with the typical agonist.

In one embodiment, the nicotinic desensitizer of formula I, or a pharmaceutically-acceptable tautomer, salt, solvate and/or ester thereof is a compound wherein (1) the agonist activity ($E_{max}$) of which for a nAChR subtype is less than about 10% of the $E_{max}$ of a typical nicotinic agonist for the nAChR subtype; (2) the inhibition of which to receptor activation of the nAChR subtype by the typical nicotinic agonist via desensitization ($IC_{50(D)}$) is less than about 10,000 nM; (3) the inhibition of which to receptor activation of the nAChR subtype by a typical nicotinic agonist ($IC_{50(A)}$) is more than about 1,000 nM when the compound is applied to the nAChR subtype simultaneously with the typical agonist; and (4) the $IC_{50(D)}$ is less than the $IC_{50(A)}$; wherein the desensitization comprises contacting the compound with the nAChR subtype for a period of time before the typical nicotinic agonist is applied to the nAChR subtype.

In another embodiment, the present invention relates to a compound of formula I or a pharmaceutically-acceptable tautomer, salt, solvate and/or ester thereof, wherein the compound is a single stereoisomer.

Selected Methods of Use

In another embodiment, the present invention relates to a method of modulating a nicotine receptor in a subject in need thereof comprising administering to the subject an effective amount of a compound of formula I, or a pharmaceutically-acceptable tautomer, salt, solvate and/or ester thereof.

In another embodiment, the present invention relates to a method of modulating a nicotine ACh receptor in a mammal comprising administering to the mammal an effective amount of a compound of formula I, or a pharmaceutically-acceptable tautomer, salt, solvate and/or ester thereof, wherein the compound, or a pharmaceutically-acceptable tautomer, salt, solvate and/or ester thereof, is administered orally.

In another embodiment, the present invention relates to a method of treating of one or more conditions or diseases associated aging, addiction, pain, obesity, schizophrenia, epilepsy, mania and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, amyotrophic lateral sclerosis, inflammation, stoke and spinal-cord injury; inflammation, inflammatory skin conditions, Chron's disease, inflammatory bowel disease, ulcerative colitis, diarrhea, endocrine disorders, thyrotoxicosis, pheochromocytoma, hypertension, and cough, comprising administering a therapeutically effective amount of a nicotinic desensitizer of formula I, or a pharmaceutically-acceptable tautomer, salt, solvate and/or ester thereof, to a subject in need thereof.

In another embodiment, the present invention relates to a method of weight control, comprising administering a therapeutically effective amount of a nicotinic desensitizer of formula I, or a pharmaceutically-acceptable tautomer, salt, solvate and/or ester thereof, to a subject in need thereof, thereby controlling the weight of said subject In another embodiment, the present invention relates to a method for treating addictions, such as nicotine, alcohol, or cocaine addiction, comprising administering a therapeutically effective amount of a nicotinic desensitizer of formula I, or a pharmaceutically-acceptable tautomer, salt, solvate and/or ester thereof, to a subject in need thereof.

In another embodiment, the present invention relates to a method for treating combination addictions, such as nicotine and alcohol, or nicotine and cocaine, comprising administering a therapeutically effective amount of a nicotinic desensitizer of formula I, or a pharmaceutically-acceptable tautomer, salt, solvate and/or ester thereof, to a subject in need thereof.

In certain embodiments, the present invention relates to any one of the aforementioned methods, wherein the compound, or a pharmaceutically-acceptable tautomer, salt, solvate and/or ester thereof, is administered intravenously, sublingually, ocularly, transdermally, rectally, vaginally, topically, intramuscularly, subcutaneously, buccally, or nasally.

In certain embodiments, the present invention relates to any one of the aforementioned methods, wherein the subject is a human.

Synthesis of Compounds

The compounds of the invention may be prepared by any conventional method useful for the preparation of analogous compounds and as described in the examples below. Starting materials for the processes described in the present patent application are known or can be prepared by known processes from commercially available materials. In addition, a compound of the invention can be converted to another compound of the invention using conventional methods. The products of the reactions described herein are isolated by conventional means such as extraction, crystallization, distillation, chromatography, and the like.

It will be appreciated by those skilled in the art that the compounds of the present invention contain several chiral centers and that such compounds exist in the form of isomers (i.e., enantiomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of D- or L-(tartrate, mandelate, or camphorsulphonate) salts for example. The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolufions", John Wiley and Sons, New York (1981).

Optical active compounds can also be prepared from optical active starting materials.

Manufacturability

The manufacturability of a potential drug candidate is an important consideration in drug development. Key parameters that need to be addressed in drug development include absorptivity, permeability, and stability. The corresponding physicochemical properties that we can adjust by modification of chemical structure are log P, polar surface area (PSA), and crystallinity, respectively. Log P is the value derived from the logarithm of the drug's partition coefficient between n-octanol and water, log ([ocantol]/[water]). Log P is an established measure of the compounds hydrophilicity that correlates well with absorptivity. For example, low hydrophilicity, and thus higher log P values, cause poor absorption of the drug. As a general rule, compounds have a reasonable probability of being absorbed if their log P values are between 2 and 5. PSA is defined as the surface sum over all polar atoms, (usually oxygen and nitrogen), also including attached hydrogen atoms. PSA correlates with the molecules ability to penetrate the cell membrane. A PSA value greater than 140 $Å^2$ usually signifies that the molecule will not be permeable to the cell membrane. In order to penetrate the blood-brain barrier, which is necessary for developing a drug to treat drug addiction, it is commonly accepted that the PSA should be less than 60 $Å^2$.

Crystallinity is an important property for a drug candidate that addresses many complex issues such as formulation. The ideal drug candidate for manufacture should have a melting point above 150° C. Drug candidates that have melting points below 100° C. typically face problems in tabletting. And, compounds that are in the liquid-state or have a melting point below 60° C. often demonstrate less-than-desired stability, requiring refrigeration. It is recommended that the melting point of a potential drug candidate be one of the first physicochemical characteristics considered.

Dosages

The dosage of any compositions of the present invention will vary depending on the symptoms, age and body weight of the patient, the nature and severity of the disorder to be treated, the route of administration, and the form of the subject composition. Any of the subject formulations may be administered in a single dose or in divided doses. Effective dosages for the compositions of the present invention may be readily determined by techniques known to those of skill in the art or as taught herein. The dosage may be selected to assuage the disorder in a subject in such a way as to provide at least partial relief if not complete relief. The skilled artisan may identify this amount as provided herein as well as by using other methods known in the art.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular composition of the present invention. This may be accomplished by routine experiment as described herein, using one or more groups of animals (preferably at least five animals per group), or in human trials if appropriate. The effectiveness of any subject composition and method of treating may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

Pharmaceutical Compositions

In accordance with the present invention, a compound of the present invention may be prepared as pharmaceutical compositions that are particularly useful for the treatment of neurodegenerative diseases or addictive disorders. Such compositions comprise a compound of the present invention or a pharmaceutically-acceptable tautomer, salt, solvate and/or ester thereof, and a pharmaceutically acceptable carrier and/or excipient.

The compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics®, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

In certain embodiments, the pharmaceutical compositions are formulated as a tablet, pill capsule or other appropriate ingestible formulation, to provide a therapeutic dose in 10 ingestible formulations or fewer. In another example, a therapeutic dose is provided in 50, 40, 30, 20, 15, 10, 5 or 3 ingestible formulations.

Kits

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

For example, the present invention also provides for kits containing at least one dose of a subject composition, and often many doses, and other materials for a treatment regimen. For example, in one embodiment, a kit of the present invention contains sufficient subject composition for from five to thirty days and optionally equipment and supplies necessary to measure one or more indices relevant to the treatment regiment. In another embodiment, kits of the present invention contain all the materials and supplies, including subject compositions, for carrying out any methods of the present invention. In still another embodiment, kits of the present invention, as described above, additionally include instructions for the use and administration of the subject compositions.

Biological Screening

Many different assay methods can be used to determine the activity of the compounds of the present invention. These assay methods include, for example, the following but also include other methods known to one of ordinary skill in the art.

Nicotinic ACh receptors in the brain are pentameric structures composed of subunits distinct from those found in skeletal muscles. The existence of eight α-subunits (α2-α9) and three β-subunits (β2-β4) in the mammalian brain has been described.

The predominant subtype with high affinity for nicotine is comprised of three α-subunits and two β-subunits.

For example, the affinity of compounds of the invention for nicotinic ACh receptors may be investigated in tests for inhibition as described below.

A. Cell Lines and Cell Culture.

The cell lines KXα3β4R2, expressing rat α3β4 nAChRs, and KXα4β2, expressing rat α4β2 nAChRs, were established previously by stably transfecting human embryonic kidney 293 cells with combinations of rat nAChR subunit genes. These cell lines are maintained in minimum essential medium supplemented with 10% fetal bovine serum, 100 units/mL penicillin G, 100 mg/mL streptomycin, and 0.7 mg/mL G418 (Geneticin) at 37° C. with 5% CO2 in a humidified incubator. The cell line SH-EP1-pcDNA-hα4β2, expressing human α4β2 nAChRs, was described previously and are available. The SH-EP1-pcDNA-hα4β2 cells are grown in Dulbecco's modified Eagle's medium supplemented with 5% fetal bovine serum, 10% horse serum, 100 units/mL penicillin G, 100 μg/mL streptomycin, 320 μg/mL hygromycin B (Calbiochem, La Jolla, Calif.), 400 units/mL Zeocin at 37° C. with 5% $CO_2$ in a humidified incubator.

B. nAChR Binding Affinity and Sub-type Selectivity Assay.

The $K_i$ values of compounds for binding to α3β4, α4β2 and other nAChR sub-types will be measured by competition experiments with [3H]epibatidine or other labeled ligands. Not intending to be bound by any one approach, one radioligand binding assay used for measuring the binding of [3H] epibatidine to nAChRs is described below.

In brief, cultured cells at above about 80% confluence will be removed from their flasks (80 cm²) with a disposable cell scraper and will be placed in 10 mL of 50 mM Tris-HCl buffer, pH 7.4, 4° C. The cell suspension will be centrifuged at 10,000 g for 5 min and the pellet will be collected. For cells undergoing prolonged treatment with nicotinic agonists during culturing, the pellet will be washed two more times by centrifugation in fresh buffer to remove residual drug. The cell pellet will then homogenized in 10 mL of buffer with a Polytron homogenizer (12-mm aggregate, 26,000 rpm, 20 s; model PT2100; Kinematica, Basel, Switzerland) and will be centrifuged at 36,000 g for 10 min at 4° C. The membrane pellet will be resuspended in fresh buffer, and aliquots of the membrane preparation equivalent to 30 to 200 μg of protein will be used for binding assays. The concentration of [3H] epibatidine used will be 100 pM for competition binding assays and 2.4 nM, which is a saturating concentration for the α4β2 receptor subtype, for measuring receptor density. Nonspecific binding will be assessed in parallel incubations in the presence of 300 μM nicotine. Bound and free ligands will be separated by vacuum filtration through Whatman GF/C filters treated with 0.5% polyethylenimine. The filter-retained radioactivity will be measured by liquid scintillation counting. Specific binding is defined as the difference between total binding and nonspecific binding. Data from saturation and competition binding assays will be analyzed using Prism 4 (GraphPad Software, San Diego, Calif.).

C. nAChR Functional Assay.

The agonist, antagonist and/or desensitizer activity of compounds of the invention can be evaluated by measuring its blockade of nicotine-stimulated 86Rb+ efflux. Not intending to be bound by any one approach, one approach to measuring functional properties of compounds at nAChRs expressed in the transfected cells using a 86Rb+ efflux assay is described below.

In brief, cells will be plated into 24-well plates coated with poly-D-lysine. The plated cells will be grown at 37° C. for 18 to 24 h to reach 85 to 95% confluence. The cells will then be incubated in growth medium (0.5 mL/well) containing 86Rb+ (2 μCi/mL) for 4 h at 37° C. The loading mixture will then be aspirated, and the cells will be washed four times with 1 mL of buffer (15 mM HEPES, 140 mM NaCl, 2 mM KCl, 1 mM $MgSO_4$, 1.8 mM $CaCl_2$, and 11 mM glucose, pH 7.4). One milliliter of buffer with or without compounds to be tested will then added to each well. After incubation for 2 min, the assay buffer will be collected for measurements of 86Rb+ released from the cells. Cells will then be lysed by adding 1 mL of 100 mM NaOH to each well, and the lysate will be collected for determination of the amount of 86Rb+ that was in the cells at the end of the efflux assay. Radioactivity of assay samples and lysates will be measured by liquid scintillation counting. Total loading (cpm) will be calculated as the sum of the assay sample and the lysate of each well. The amount of 86Rb+ efflux will be expressed as a percentage of 86Rb+ loaded. Stimulated 86Rb+ efflux is defined as the difference between efflux in the presence and absence of nicotine. For obtaining an $IC_{50}$ value, inhibition curves are constructed in which different concentrations of an antagonist are included in the assay to inhibit efflux stimulated by 100 μM nicotine. $IC_{50}$ values will be determined by nonlinear least-squares regression analyses (GraphPad Software).

PCT Patent App. Pub. No. WO 2008/011484 A2 to Xiao et al, hereby incorporated by reference in its entirety, compounds showing high selectivity to α4β2 nChRs in binding assays, agonist tests, antagonist tests and desensitizer tests were advanced to further tests in animal models. A similar approach can be taken with the compounds of the instant invention.

D. Measurement of Desensitization.

Not intending to be bound by any one method, desensitization may be measured, for example, by the method described below.

The desensitization of the nAChR will be measured by comparing the effects of compounds of the invention on nAChR channel function with or without a 10 min pretreatment. The 86Rb+ efflux assays in cells expressing human α4β2 and rat α3β4 nAChRs are carried out as described above. Cells are either preincubated with buffer alone and then exposed simultaneously to 100 μM nicotine and the indicated concentration of drug (0 min, no pretreatment group), or the cells are preincubated for 10 min at a certain concentration of drug alone and then exposed to 100 μM nicotine plus the drug (10 min, pretreatment group). Concentration-effect curves will be calculated for three to seven independent experiments.

DEFINITIONS

For purposes of this invention, the chemical elements are identified in accordance with the Periodic Table of the Elements, CAS version, Handbook of Chemistry and Physics, 67th Ed., 1986-87, inside cover.

The articles "a" and "an" are used herein to refer to one or to more than one (i.e., to at least one) of the grammatical object of the article. By way of example, "an element" means one element or more than one element.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "arylalkoxy" and "heteroarylalkoxy" as used herein, means an aryl group or heteroaryl group, as defined herein, appended to the parent molecular moiety through an alkoxy group, as defined herein. Representative examples of arylalkoxy include, but are not limited to, 2-chlorophenylmethoxy, 3-trifluoromethylethoxy, and 2,3-methylmethoxy.

The term "arylalkyl" as used herein, means an aryl group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkyl" means a hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Representative examples of alkyl include, but are not limited to, methyl, ethyl, n-propyl, iso-propyl, n-butyl, sec-butyl, iso-butyl, tert-butyl, n-pentyl, iso-pentyl, neopentyl, and n-hexyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" and "arylcarbonyloxy" as used herein, means an alkylcarbonyl or arylcarbonyl group, as defined herein, appended to the parent molecular moiety through an oxygen atom. Other groups, such as "heteroarylcarbonyloxy" are likewise defined. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkylsulfonyl" and "arylsulfonyl" as used herein, means an alkyl or arly group, as defined herein, appended to the parent molecular moiety through a sulfonyl group, as defined herein. Other groups, such as "heterarylsulfonyl" are likewise defined. Representative examples of alkylsulfonyl include, but are not limited to, methylsulfonyl and ethylsulfonyl. The term "arylsulfonyl" as used herein, means an aryl group, as defined herein, appended to the parent molecular moiety through a sulfonyl group, as defined herein. An example of an alkylsulfonyl is tosyl, which is p-toluenesulfonyl ($CH_3C_6H_4SO_2$—); and an example of an arylsulfonyl is mesyl, which is methylsulfonyl ($CH_3SO_2$—).

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino" as used herein, refers to —$NH_2$. The term "alkylamino" refers to an alkyl group, as defined herein, appended to the parent molecular moiety through an —N(H)— group. The term "alkylcarbonylamino" refers to an alkylcarbonyl group, as defined herein, appended to the parent molecular moiety through an —N(H)— group. The term "dialkylamino" refers to two alkyl group (which can be the same or different), as defined herein, both appended to the parent molecular moiety through a nitrogen atom. Other groups, such as "arylamino" are likewise defined. Representative examples include, but are not limited to methylamino, acetylamino, and acetylmethylamino.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "aryl," as used herein, refers to an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like. The aryl groups of the present invention can be optionally substituted with one, two, three, four, or five substituents independently selected from the group consisting of alkenyl, alkoxy, alkoxycarbonyl, alkoxysulfonyl, alkyl, alkylcarbonyl, alkylcarbonyloxy, alkylsulfonyl, alkylthio, alkynyl, amino, carboxy, cyano, formyl, halo, haloalkoxy, haloalkyl, hydroxyl, hydroxyalkyl, mercapto, nitro, silyl and silyloxy.

The term "arylene," is art-recognized, and as used herein, pertains to a bidentate moiety obtained by removing two hydrogen atoms of an aryl ring, as defined above.

The term "arylalkyl" or "aralkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-yl-ethyl.

The term "arylalkoxy" or "arylalkyloxy" as used herein, means an arylalkyl group, as defined herein, appended to the parent molecular moiety through an oxygen. Other groups, such as "heteraryloxy" are likewise defined.

The term "arylalkylthio" and "heteroarylalkylthio" as used herein, means an arylalkyl or a heteroarylalkyl group, as defined herein, appended to the parent molecular moiety through an sulfur. Other groups, such as "alkylaryloxy" are likewise defined.

The term "arylalkenyl" as used herein, means an aryl group, as defined herein, appended to the parent molecular moiety through an alkenyl group. A representative example is phenylethylenyl.

The term "arylalkynyl" as used herein, means an aryl group, as defined herein, appended to the parent molecular moiety through an alkynyl group. A representative example is phenylethynyl.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "arylcarbonylalkyl" as used herein, means an arylcarbonyl group, as defined herein, bound to the parent molecule through an alkyl group, as defined herein.

The term "arylcarbonylalkoxy" as used herein, means an arylcarbonylalkyl group, as defined herein, bound to the parent molecule through an oxygen.

The term "aryloxy" as used herein, means an aryl group, as defined herein, appended to the parent molecular moiety through an oxygen. The term "heteroaryloxy" as used herein, means a heteroaryl group, as defined herein, appended to the parent molecular moiety through an oxygen.

The term "carbonyl" as used herein, means a —C(=O)— group.

The term "carboxy" as used herein, means a —CO$_2$H group.

The term "cycloalkyl" as used herein, means monocyclic or multicyclic (e.g., bicyclic, tricyclic, etc.) hydrocarbons containing from 3 to 12 carbon atoms that is completely saturated or has one or more unsaturated bonds but does not amount to an aromatic group. Examples of a cycloalkyl group include cyclopropyl, cyclobutyl, cyclopentyl, cyclopentenyl, cyclohexyl and cyclohexenyl.

The term "cycloalkoxy" as used herein, means a cycloalkyl group, as defined herein, appended to the parent molecular moiety through an oxygen.

The term "cyano" as used herein, means a —CN group.

The term "formyl" as used herein, means a —C(=O)H group.

The term "halo" or "halogen" means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl", as used herein, include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, or 3 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amino, carboxy, cyano, formyl, halo, haloalkoxy, haloalkyl, hydroxyl, hydroxyalkyl, mercapto, nitro, silyl and silyloxy. When the heterocylyl contains a nitrogen, the nitrogen may likewise be substituted.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, or 3 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amino, carboxy, cyano, formyl, halo, haloalkoxy, haloalkyl, hydroxyl, hydroxyalkyl, mercapto, nitro, silyl and silyloxy.

The term "heteroarylene," is art-recognized, and as used herein, pertains to a bidentate moiety obtained by removing two hydrogen atoms of a heteroaryl ring, as defined above.

The term "heteroarylalkyl" or "heteroaralkyl" as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —$NO_2$ group.

The term "silyl" as used herein includes hydrocarbyl derivatives of the silyl ($H_3Si$—) group (i.e., (hydrocarbyl)$_3$Si—), wherein a hydrocarbyl groups are univalent groups formed by removing a hydrogen atom from a hydrocarbon, e.g., ethyl, phenyl, pyridinyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The term "sulfonyl" as used herein, means a —S(=O)$_2$— group.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "inverse agonist" refers to a compound that binds to a constitutively active receptor site and reduces its physiological function.

The term "competitive antagonist" refers to a compound that binds to a receptor site; its effects can be overcome by increased concentration of the agonist.

The term "partial agonist" refers to a compound that binds to a receptor site but does not produce the maximal effect regardless of its concentration.

The term "ligand" refers to a compound that binds at the receptor site; and as used herein refers to any organic chemical compound. Examples of ligands include, but are not limited to a peptide, a protein, a nucleotide or its fragment, a polymer, and a natural or synthetic small molecule having a molecular weight of about 1,500 daltons or less.

The term "nicotinic desensitizer" as used herein refers to a ligand that can desensitize a nicotinic acetylcholine receptor (nAChR) in a significant manner. More specifically, a nicotinic desensitizer is a ligand that has the following characteristics: (1) has high binding affinity to a nicotinic acetylcholine receptor (nAChR) subtype in binding assays; (2) does not have full agonist activity to the receptor subtype; (3) does not potently inhibit channel activations by an agonist if applied to a nAChR with the agonist simultaneously; and (4) potently inhibits channel activations by an agonist if the receptor is pre-incubated with the ligand for a period of time before the agonist is applied. Preferably, a nicotinic desensitizer is a ligand that has all of the above described characteristics. It should be understood that the term "nicotinic desensitizer" as used herein includes all tautomers, stereoisomers, diastereomer, and enantiomers of a nicotinic desensitizer having a particular chemical structure.

"Ester thereof" means any ester of a nicotinic desensitizer in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The term "ester thereof" includes but is not limited to pharmaceutically acceptable esters thereof.

"Salt thereof" means any acid and/or base addition salt of a nicotinic desensitizer according to the invention; preferably a pharmaceutically acceptable salt thereof.

"Solvate thereof" means a nicotinic desensitizer formed by solvation (the combination of solvent molecules with molecules or ions of the solute), or an aggregate that consists of a solute ion or molecule (the nicotinic desensitizer) with one or more solvent molecules.

"Pharmaceutically acceptable salt" means a salt of a nicotinic desensitizer which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. Where applicable and compatible with the chemical properties of the nicotinic desensitizer, the term includes pharmaceutically-acceptable acid addition salts and pharmaceutically-acceptable base addition salts. Lists of suitable salts are found in, e.g., S. M. Birge et al., J. Pharm. ScL1 1977, 66, pp. 1-19.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —C(O)$_2$H or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$) alkyl.

Other exemplary pro-drugs release an alcohol or optionally substituted amine of a compound of the invention wherein the free hydrogen of a hydroxyl substituent or optionally substituted amine substituent is replaced by ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyl-oxymethyl, N—($C_1$-$C_6$)alkoxycarbonylamino-methyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O($C_1$-$C_6$)alkyl)$_2$ or glycosyl (the radical resulting from detachment of the hydroxyl of the hemiacetal of a carbohydrate).

"Treating" is used herein to refer to any treatment of, or prevention of, or inhibition of a disorder or disease in a subject and includes by way of example: (a) preventing the disease or disorder from occurring in a subject that may be predisposed to the disease or disorder, but has not yet been diagnosed as having it; (b) inhibiting the disease or disorder, i.e., arresting its progression; or (c) relieving or ameliorating the disease or disorder, i.e., causing regression.

EXEMPLIFICATION

The invention now being generally described, it will be more readily understood by reference to the following examples which are included merely for purposes of illustration of certain aspects and embodiments of the present invention, and are not intended to limit the invention.

Example 1

Gram-Scale Synthesis of Sazetidine A

A gram-scale synthesis of sazetidine A is outlined in FIG. 1a. The Boc-protected azidityl methyl alcohol 2 and 3-bromo-5-hydroxy pyridine (3) are both commercially available. Treatment with PPh$_3$ and DEAD according to the Mitsunobu protocol formed ether derivative 4 in 70% yield. Palladium-mediated coupling of the bromo-substituted pyridine 4 with 5-hexyn-1-ol under modified Sonogashira conditions furnished Boc-protected sazetidine A in 73% yield. Deprotection of the Boc-group with HCl was expected to give sazetidine A in salt form as published in the literature. However, after several attempts, it was found that the HCl salt, especially on larger scale, was a white solid that could be obtained in only moderate yield by a tedious filtration under an inert atmosphere. Exposure of the material to air immediately resulted in decomposition of the material to a yellow-brown wet solid.

Therefore, in order to obtain gram quantities of pure sazetidine A, it was found that it was necessary to treat the deprotected material immediately with NH$_4$OH and then isolated the free base of sazetidine A. This product was then taken up in an aqueous solution of HCl to give a solution of the HCl salt of sazetidine A. This modified method gives purer material and was indeed found to be more potent than that reported in the literature.

Example 2

Design and Synthesis of Triazetidine O, a Triazole Analog of Sazetidine A

As outlined above, for the purposes of drug development it is necessary for a drug to be manufacturable. Crystallinity is a physicochemical property that is recommended for successful development of a drug candidate. Unlike log P and PSA, there is no reliable computational method to predict that a compound will be crystalline. As biaryl compounds are often isolated in crystalline form, it was hypothesized that by replacing the alkynyl group in sazetidine A with a small aryl bioisostere, the selectivity and potency of sazetidine A would be retained and the compound would be crystalline. For example, the alkynyl group can be replaced with a triazole group to give a new analog. The synthesis of such an analog (herein called triazetidine O) is outlined in FIG. 1b.

The copper I mediated conversion of 3-Bromo-5-hydroxy pyridine (3) to 3-azido-5-hydroxy pyridine (6) was accomplished in 40% yield according to the method of Liang and co-workers. Etherification with alcohol 2 under Mitsunobu conditions then gave the product 7 in 54% yield. Coupling of the azide functionality with 5-hexyn-1-ol by [3+2]Huisgen cycloaddition was accomplished using the Sharpless click chemistry methodology to give protected triazetidine O in 99% yield. Deprotection with HCl-Et$_2$O solution followed by a basic work-up with NH$_4$OH gave triazetidine O as a white solid (mp=180-181° C.).

The physical properties of triazetidine O is a major improvement over sazetidine A. As noted above, a melting point of greater than 150° C. is necessary for a drug to be manufacturable, and triazetidine O meets this requirement.

NMR and MS data for triazetidine O: $^1$H NMR (CD$_3$OD): 1.58-1.65 (m, 2H), 1.76-1.84 (m, 2H), 1.91 (s, 1H), 2.67-2.70 (m, 2H), 2.82 (t, J=7.4 Hz, 2H), 3.28-3.30 (m, 2H), 3.60 (t, J=6.5 Hz, 2H), 4.08-4.16 (m, 2H), 4.51-4.63 (m, 2H), 8.05-8.07 (m, 1H), 8.48 (d, J=2.4 Hz, 1H), 8.57 (s, 1H), 8.77 (d, J=1.9 Hz, 1H); $^{13}$C NMR: 20.4, 24.6, 25.3, 31.6, 43.4, 58.9, 61.1, 67.3, 113.5, 120.6, 133.4, 134.5, 137.7, 149.0, 155.0. TOF-MS obsd 304.1765 (M+H)+, calcd 303.1695 [M=C$_{15}$H$_{20}$N$_2$O$_2$].

Example 3

Pharmacological Comparisons of Sazetidine A and Triazetidine O

The selectivity of triazetidine O was evaluated by comparing its affinity for α4β2 and α3β4 nAChRs (FIG. 1c). The results reveal that the triazole group is an active isostere of the alkyne. The K$_i$ for triazetidine O is 3.51 nM for the α4β2 receptor and 62,000 nM for the α3β4, reflecting a 17,692-fold selectivity for the α4β2 receptor. Triazetidine O is also a potent desensitizer of α4β2 with an IC$_{50}$ of 100 nM. The relative affinity of triazetidine O for the α4β2 receptor in comparison with sazetidine A is decreased from 0.41 nM to 3.51 nM. Regardless, of the decreased activity, triazetidine O remains a sub-nanomolar ligand and maintains incredible selectivity for the α4β2 receptor. And, triazetidine O has superior physicochemical properties than sazetidine A, making it a suitable candidate for further drug development Altogether, triazetidine O represents a new class of soluble, crystalline, potent, α4β2-selective desensitizers that has the qualities necessary for manufacture.

Example 4

Calculation of Log P and PSA

As mentioned above, log P and PSA can be reasonably estimated by computational calculations (the calculated log P is designated as clog P). The manufacturability of our proposed drug candidates depended on crystallinity, which was successfully addressed by synthesizing triazetidine O, an analog of sazetidine that incorporates a biaryl structure. The log P and PSA values are concerned with the efficacy of the drug in vivo. The target log P-values for our purposes for improved absorptivity is between 2 and 5. The target PSA for increased penetration of the blood-brain barrier is about 60 Å$^2$. Triazetidine O is a major improvement over sazetidine A for manufacturability. However, further optimization is necessary considering the relatively poor efficacy predicted for triazetidine O considering its clog P is calculated to be 0.80 and its PSA is 156.6 Å$^2$.

FIG. 2 represents the computed molecular weight, clog P, and PSA for a representative set of molecules. Note that these analogs address the deficient clog P and PSA values for triazetidine O, our lead for a manufacturable drug candidate.

Figure 4:
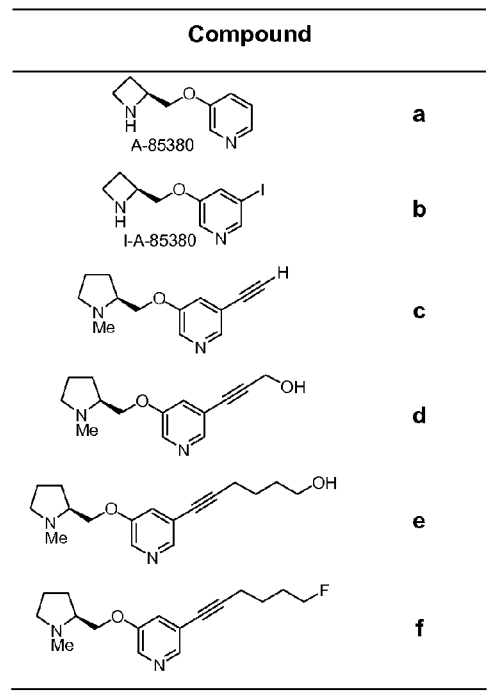
FIG. 4 depicts the effect of alkyl chain substituent on selectivity.

The PSA of a molecule can be used to predict its ability to cross the blood-brain barrier. Sazetidine A suffers from a relatively high PSA of 113.5 Å$^2$, suggesting a relatively low efficacy in vivo. In FIG. 4, the most active selective analog (last compound in the series) shows a similar pharmacological profile as sazetidine A, but has several structural modifications. Namely, the hydroxyl of the alkyl chain is replaced by a fluorine atom, the 4-member azitidinyl ring is replaced with a 5-member pyrrolidine ring, and the amine nitrogen is capped with a methyl group. This compound was reported to be an oil, and thus not suitable for further development. These changes resulted in a reduced PSA value of this molecule, while maintaining remarkable nAChR-subtype selectivity and potency. These results can be used to design new analogs that are predicted to have better blood-brain barrier penetration than sazetidine A.

Figure 5:
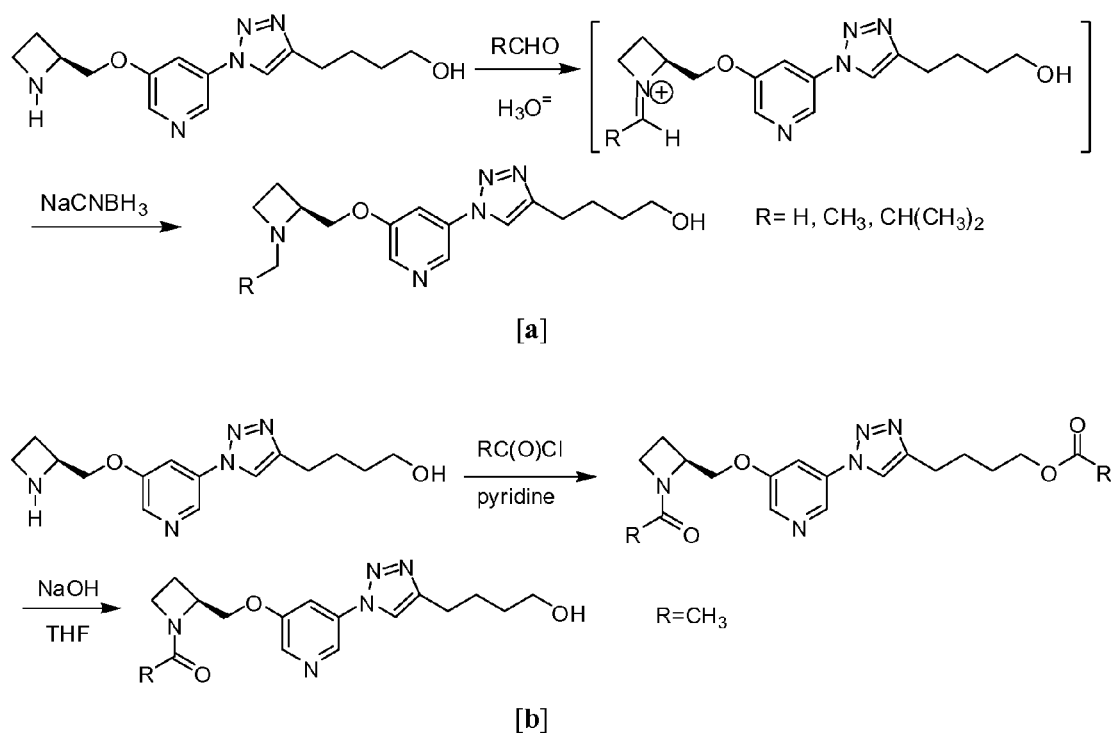
FIG. 5 depicts one route to the preparation of compounds of the invention with N-substituted azidityl moieties.

Initially, triazetidine O analogs will be modified by capping the amine nitrogen with a methyl, ethyl, isobutyl, and acetate. Reductive alkylation methods by condensation of the amine nitrogen atom with the appropriate aldehyde followed by reduction of the corresponding imine with NaCNBH$_3$ as shown in FIG. 5a will give the tertiary amine. Capping with an acetate group will be accomplished simply by treating the free amine with acetyl chloride to give the bis-acetylated product, which is also a reasonable analog for testing. Formation of the free hydroxyl will be performed by treatment with aqueous NaOH in THF (FIG. 5b).

Figure 6:
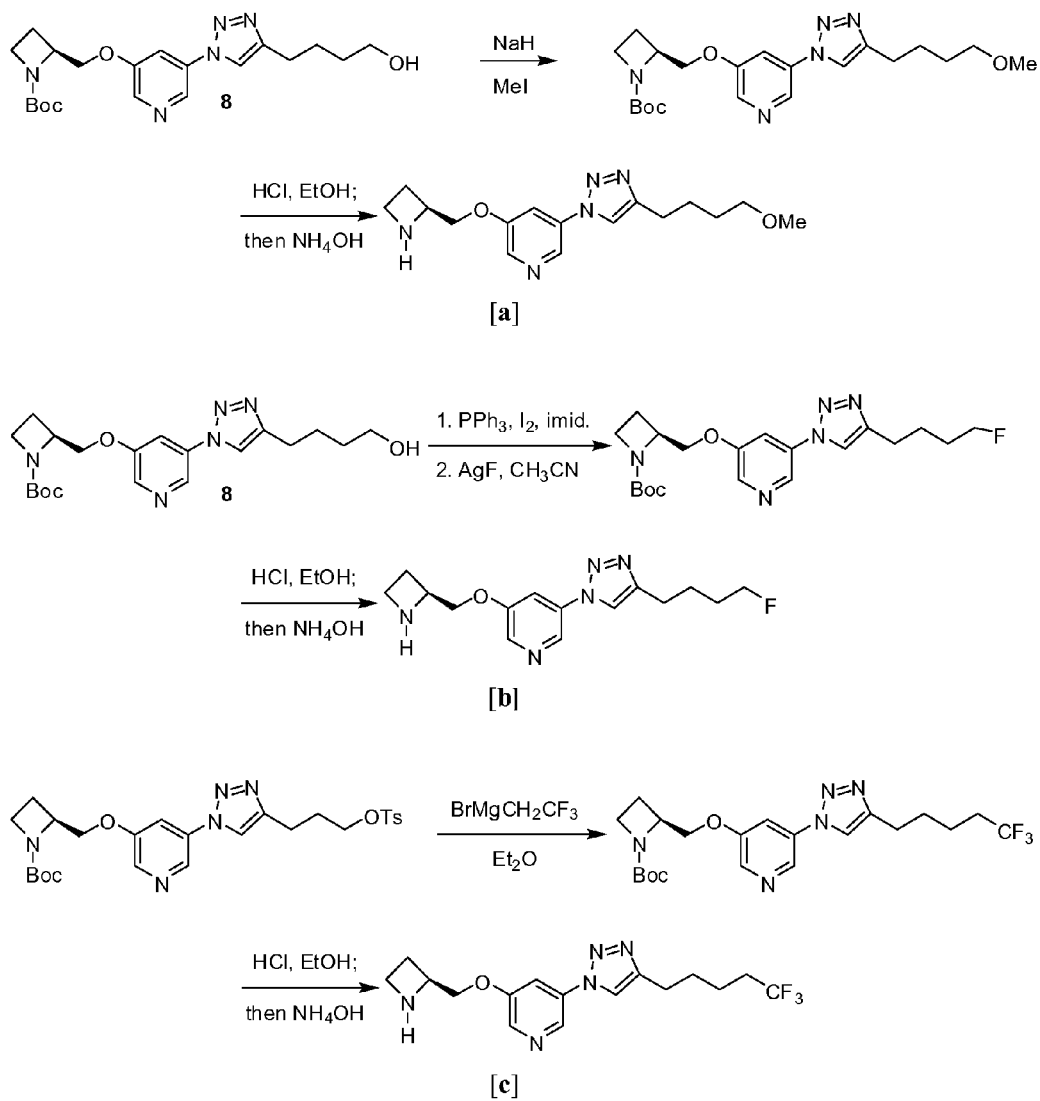
FIG. 6 depicts routes for transforming a hydroxyl to methoxy-, fluoro- and trifluoromethyl-substituted compounds of the invention.

Transformations at the hydroxyl group will require using the Boc-protected precursor 8. First, the substrate will be converted to the methyl ether by treatment with MeI under basic conditions. Acid-catalyzed removal of the Boc-protecting group followed by a basic work-up gives the product (FIG. 6a). Conversion to the mono-fluoro derivative will be accomplished by initial iodination, followed by treatment with AgF to give the fluorinated carbon. Treatment with acid followed by a basic work-up will then give the desired product (FIG. 6b). And, finally a CF$_3$ group could be introduced by addition of a Grignard reagent that contains the CF$_3$ group to a tosylated derivative of precursor 8 with a shortened carbon chain. As before, treatment with acid followed by a basic work-up would give the product with a terminal CF$_3$-group (FIG. 6c).

Each of the proposed operations results in a considerable lowering of the calculated PSA. These analogs will be tested for nAChR binding-affinity, α4β2 and α3β4 sub-type selectivity, nAChR desensitization (methods described herein).

Example 5

Preparation of Crystalline Compounds

Figure 3:
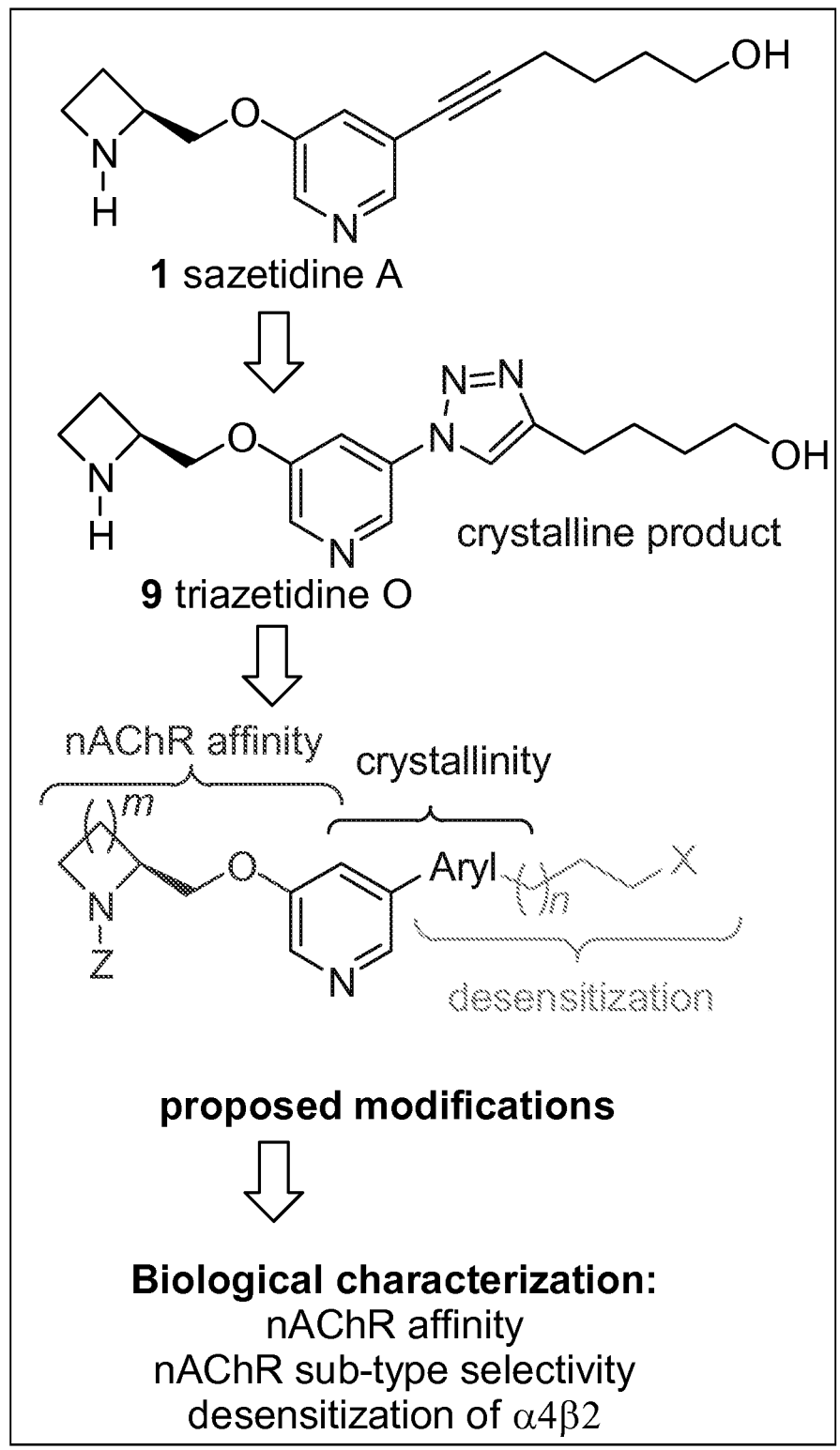
FIG. 3 depicts the progression that guided the development of selected compounds of the invention.

Crystallinity has been achieved by replacing the alkynyl group with a triazole ring system, as noted above. Although, the triazole ring proved to be a bioisostere of the alkyne, the resulting analog had an approximately 10-fold decrease in K$_i$. In order to investigate whether other aromatic groups can give compounds with comparable activity as sazetidine A and maintain crystallinity, a series of biaryl analogs of triazetidine O will be synthesized. Synthetic methods to replace the aryl group shown in FIG. 3 will require a bifunctional handle on the aryl group. Homologation of our aryl group can be effected by Pd-mediated Negishi coupling of intermediate 4 with an appropriate aryl zinc reagent (FIG. 7a).

The bifunctional handle envisioned for the synthesis of the zinc reagent is iodo-substituted aryl aldehydes. The alkyl chain of sazetidine A can be appended by Wittig reaction of the aldehyde with the phosphonium salt of 4-iodo-1-benzyloxybutane (10). Formation of the zinc reagent by the method of Knochel would give the cross-coupling reagent for the palladium-mediated connection with aryl-bromide 4 (FIG. 7b). Debenzylation would give the free alcohol, which also effects reduction of the olefin to the alkane. Deprotection of the Boc-group, basic work-up, and reductive amination with formaldehyde would give the desired analogs as outlined in FIG. 7a.

A representative series of these organozinc reagents that will be used for the Negishi reaction is given in FIG. 8 with the corresponding analogs that they will provide.

Example 6

Preparation of Compounds with Modified Alkyl Chains

In comparison with A-85380, 5-iodo-substitution on the pyridine ring of A-85380 results in an increased α3β4:α4β2 ratio of K$_i$ values signifying more selectivity for the α4β2 subtype (see FIG. 4). The alkyl chain of sazetidine A extends from the 5-position of the pyridine ring, because steric bulk in this region was expected to increase selectivity for α4β2. As expected, 5-alkynyl derivatives showed increasing selectivity with increasing length of the carbon chain (FIG. 4). A computational study on selective binding modes to the α4β2 subtype suggests that the nitrogen-containing groups should bind to the α subunit, whereas an aliphatic appendage is expected to interact with non-conserved residues in the β subunit. Based on the limited data available, it is predicted that this alkyl chain is involved with important interactions with the receptor.

Figure 9:
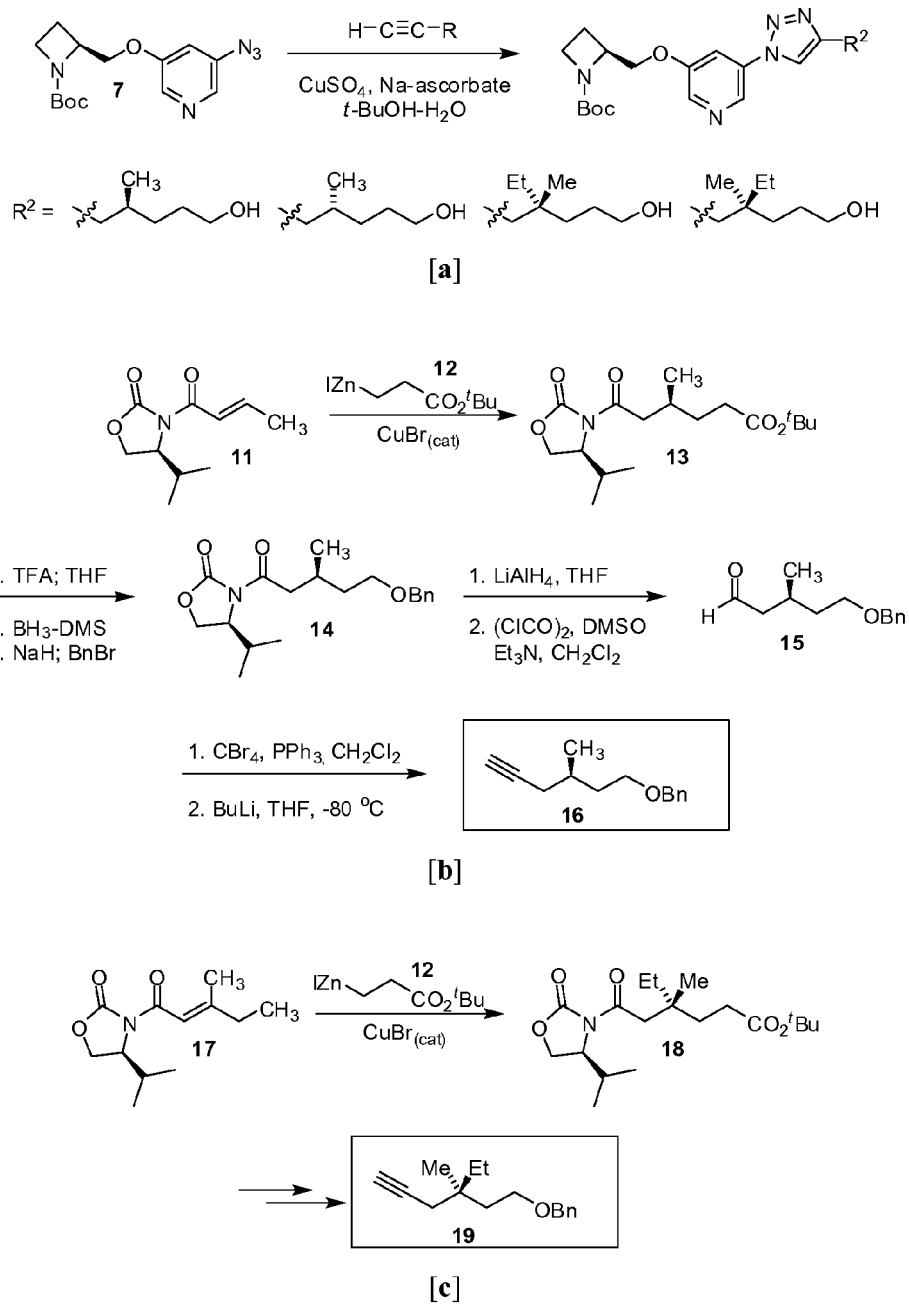
FIG. 9 depicts a route to preparing non-racemic triazole containing compounds using non-racemic alkynes; and two routes to the preparation of non-racemic alkynes that could be used in the triazole synthesis.

First, the importance of stereochemistry in the putative β subunit binding domain that interacts with the aliphatic chain will be explored. Following the method for triazole synthesis provided above, a series of non-racemic alkynes will serve as coupling partners with azide 7 (FIG. 9a).

Synthesis of the alkynyl precursors will involve utilization of a modified method involving asymmetric Michael addition to oxazolidinone 11 as described by Hruby with functionalized organozinc reagent 12. Knochel has elegantly described the use of organozinc reagents that contain an ester functionality as versatile nucleophiles for asymmetric additions into aldehydes. However, it is believed that this reagent has not previously been used in asymmetric Michael additions. This strategy represents a new method for the synthesis of a remote methyl stereocenter (FIG. 9b). Elaboration to the alkyne involves selective removal of the t-Bu group with TFA, borane-mediated reduction of the resulting carboxylic acid, and benzyl protection of the alcohol to give compound 14. Reduction of the oxazolidinone with LiAlH₄, followed by Swern oxidation gives the aldehyde 15. Corey-Fuchs alkynylation then gives the requisite alkyne 16.

This type of reaction also lends well to setting quarternary carbons, a motif that remains challenging in organic synthesis. As shown in FIG. 9c, addition of the functionalized organozinc reagent into the tri-substituted olefin 17 gives product 18, which can then be elaborated to alkyne 19 as described above.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein.

We claim:
1. A compound of formula I:

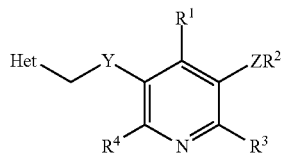

or a pharmaceutically acceptable tautomer or salt thereof, wherein
Y is O or S;
Het is

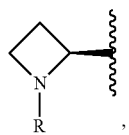

wherein R is selected from the group consisting of hydrogen and alkyl;
Z is

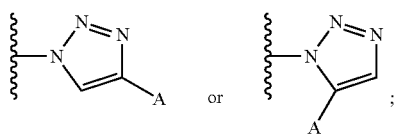

A is a bond to $R^2$;
$R^1$ is hydrogen, halo or alkyl;
$R^3$ is hydrogen, halo or alkyl;
$R^4$ is hydrogen, halo or alkyl;
$R^2$ is

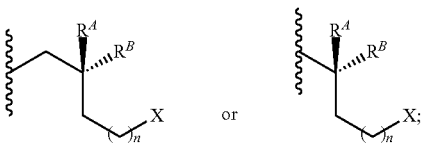

$R^A$ is hydrogen or alkyl;
$R^B$ is hydrogen or alkyl;
n is 0, 1, 2, 3 or 4; and
X is hydrogen, halo, hydroxyl, alkyloxy, trifluoromethyl or alkyl.
2. The compound of claim 1, wherein Y is O.
3. The compound of claim 1, wherein R is hydrogen.
4. The compound of claim 1, wherein $R^1$ is hydrogen; $R^3$ is hydrogen; and $R^4$ is hydrogen.
5. The compound of claim 4, wherein $R^2$ is

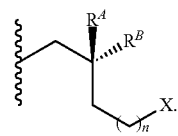

6. The compound of claim 4, wherein $R^2$ is

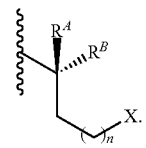

7. The compound of claim 2 or 6, wherein n is 1.
8. The compound of claim 6, wherein X is halo, hydroxyl, or trifluoromethyl.
9. The compound of claim 8, wherein X is fluoro or hydroxyl.
10. The compound of claim 8 or 9, wherein $R^A$ is hydrogen.
11. The compound of claim 10, wherein $R^B$ is hydrogen.
12. A compound selected from the group consisting of:

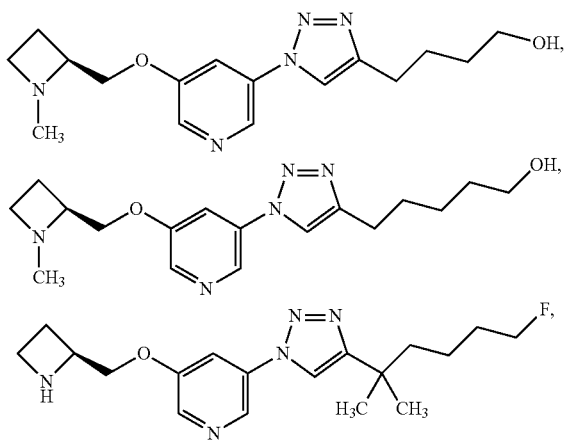

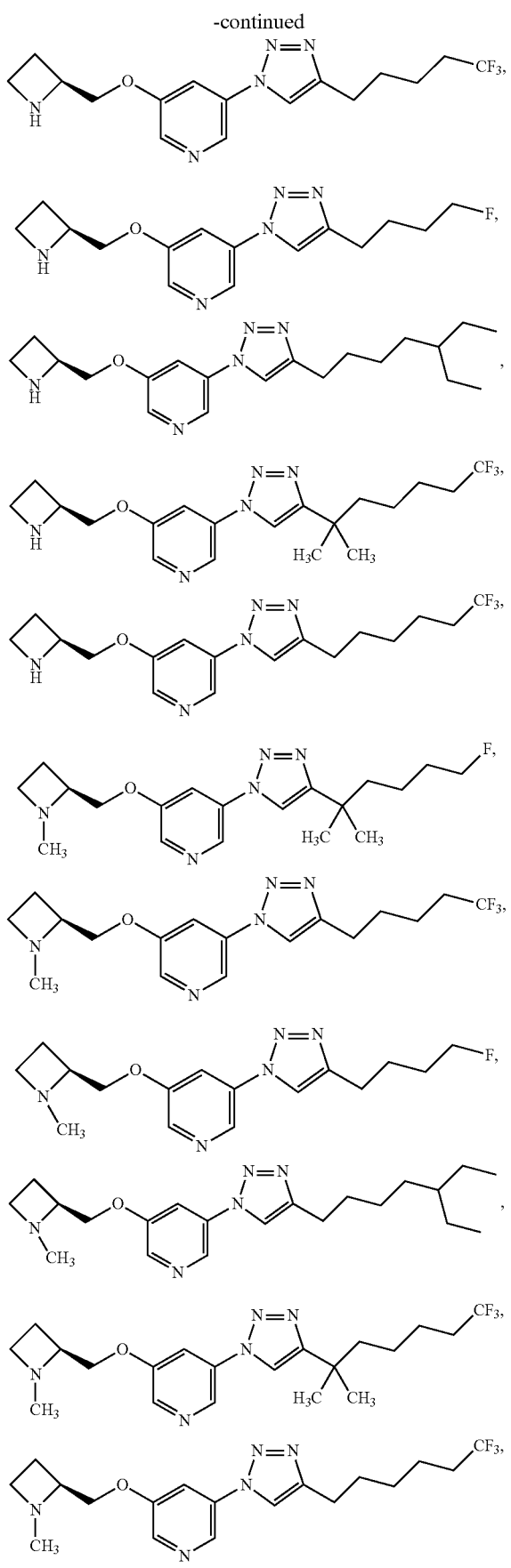
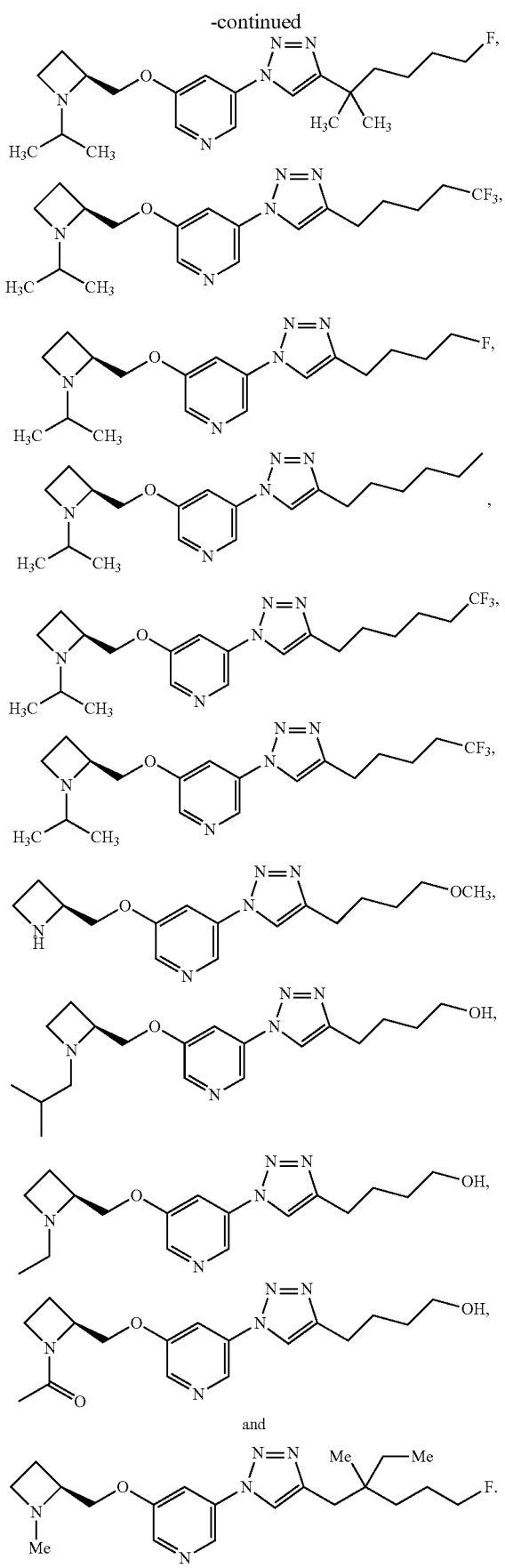

13. A pharmaceutical composition comprising a compound of claim 1 and a pharmaceutically acceptable excipient.

14. The compound

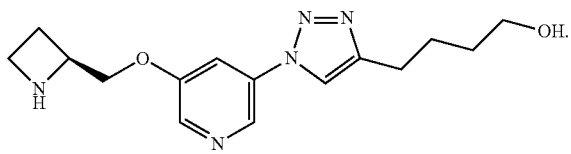 [SMILES: OCCCCc1cn(-c2cncc(OC[C@@H]3CCN3)c2)nn1]

15. A pharmaceutical composition comprising the compound of claim 14, or a pharmaceutically acceptable tautomer or salt thereof, and a pharmaceutically acceptable excipient.

16. The compound

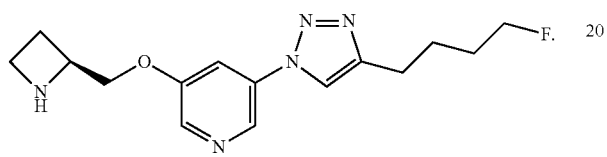

17. A pharmaceutical composition comprising the compound of claim 16, or a pharmaceutically acceptable tautomer or salt thereof, and a pharmaceutically acceptable excipient.

* * * * *